(12) United States Patent
Leiris et al.

(10) Patent No.: US 12,286,411 B2
(45) Date of Patent: Apr. 29, 2025

(54) INDANE DERIVATIVES FOR USE IN THE TREATMENT OF BACTERIAL INFECTION

(71) Applicant: Antabio SAS, Labege (FR)

(72) Inventors: Simon Leiris, Labege (FR); David Thomas Davies, Labege (FR); Martin Everett, Labege (FR); Nicolas Sprynski, Labege (FR); Lilha Beyria, Labege (FR); Thomas David Pallin, Margate (GB); Andrew Peter Cridland, Margate (GB); Toby Jonathan Blench, Margate (GB); Richard Leonard Elliott, Margate (GB); David Edward Clark, Margate (GB)

(73) Assignee: Antabio SAS, Paris (FR)

( * ) Notice: Subject to any disclaimer, the term of this patent is extended or adjusted under 35 U.S.C. 154(b) by 941 days.

(21) Appl. No.: 17/277,649

(22) PCT Filed: Jul. 25, 2019

(86) PCT No.: PCT/EP2019/070115
§ 371 (c)(1),
(2) Date: Mar. 18, 2021

(87) PCT Pub. No.: WO2020/064173
PCT Pub. Date: Apr. 2, 2020

(65) Prior Publication Data
US 2021/0347748 A1    Nov. 11, 2021

(30) Foreign Application Priority Data

Sep. 25, 2018  (EP) .................... 18290106
Sep. 26, 2018  (EP) .................... 18290104
Sep. 27, 2018  (EP) .................... 18197365

(51) Int. Cl.
| C07D 277/64 | (2006.01) |
| A61K 45/06 | (2006.01) |
| A61P 31/04 | (2006.01) |
| C07D 417/06 | (2006.01) |
| C07D 417/12 | (2006.01) |

(52) U.S. Cl.
CPC ............ *C07D 277/64* (2013.01); *A61K 45/06* (2013.01); *A61P 31/04* (2018.01); *C07D 417/06* (2013.01); *C07D 417/12* (2013.01)

(58) Field of Classification Search
CPC .............. A61K 31/4184; A61K 31/195; A61K 31/343; A61K 31/357; A61K 31/381; A61K 31/402; A61K 31/404; A61K 31/415; A61K 31/423; A61K 31/426; A61K 31/437; A61K 31/472; A61K 31/496; A61K 45/06; C07D 207/14; C07D 209/14; C07D 213/56; C07D 231/12; C07D 235/14; C07D 235/16
See application file for complete search history.

(56) References Cited

U.S. PATENT DOCUMENTS

| 5,457,196 A | 10/1995 | Warshawsky et al. |
| 5,532,257 A | 7/1996 | Hase et al. |
| 5,688,818 A | 11/1997 | Hosono et al. |
| 10,934,302 B1 | 3/2021 | Taylor et al. |
| 2002/0128290 A1 | 9/2002 | Ohshima et al. |
| 2004/0180941 A1 | 9/2004 | Hepworth |
| 2006/0223830 A1 | 10/2006 | De Nanteuil et al. |
| 2010/0113462 A1 | 5/2010 | Caulfield et al. |
| 2012/0122764 A1 | 5/2012 | Karki et al. |
| 2015/0282483 A1 | 10/2015 | Sawada et al. |
| 2021/0347748 A1 | 11/2021 | Leiris et al. |

(Continued)

FOREIGN PATENT DOCUMENTS

| DE | 43 39 198 | 5/1995 |
| EP | 0 117 429 | 9/1984 |

(Continued)

OTHER PUBLICATIONS

Cathcart et al., "Novel Inhibitors of the *Pseudomonas aeruginosa* Virulence Factor LasB: a Potential Therapeutic Approach for the Attenuation of Virulence Mechanisms in Pseudomonal Infection," *Antimicrobial Agents and Chemotherapy* 55(6):2670-2678, 2011.

Desroy et al., "Novel HldE-K Inhibitors Leading to Attenuated Gram Negative Bacterial Virulence," *Journal of Medicinal Chemistry* 56:1418-1430, 2013.

Ding et al, "Synthesis and investigation of novel 6-(1,2,3-triazol-4-yl)-4-aminoquinazolin derivatives possessing hydroxamic acid moiety for cancer therapy," *Bioorganic & Medicinal Chemistry* 25:27-37, 2017.

Ganeshpurkar et al., "Strategies for the Synthesis of Hydroxamic Acids," *Current Organic Synthesis* 15(2):154-165, 2018.

(Continued)

*Primary Examiner* — Erich A Leeser
(74) *Attorney, Agent, or Firm* — Klarquist Sparkman, LLP

(57) ABSTRACT

The invention relates to an indane compound according to Formula (I), or a pharmaceutically acceptable salt thereof,

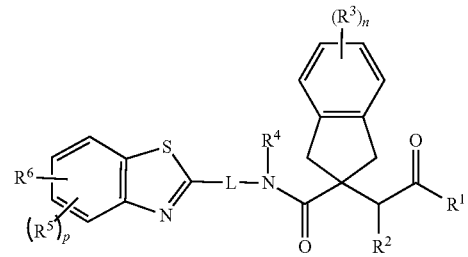

[FORMULA (I)]

wherein $R^1$, $R^2$, $R^3$, $R^4$, $R^5$, $R^6$, L, n and p are as defined herein. The compounds are useful for treating antibacterial infection either as stand-alone antibiotics, or in combination with further antibiotics.

14 Claims, 2 Drawing Sheets

(56) References Cited

U.S. PATENT DOCUMENTS

2022/0041560 A1 2/2022 Selby et al.
2022/0112169 A1* 4/2022 Leiris .................. C07D 277/64

FOREIGN PATENT DOCUMENTS

| JP | H 11-130761 | 5/1995 |
|----|----|----|
| WO | WO 98/003202 | 1/1998 |
| WO | WO 2003/011842 | 2/2003 |
| WO | WO 2003/089418 | 10/2003 |
| WO | WO 2003/094889 | 11/2003 |
| WO | WO 2005/016249 | 2/2005 |
| WO | WO 2006/029153 | 3/2006 |
| WO | WO 2006/122250 | 11/2006 |
| WO | WO 2006/125511 | 11/2006 |
| WO | WO 2007/031860 | 3/2007 |
| WO | WO 2007/073503 | 6/2007 |
| WO | WO 2007/099423 | 9/2007 |
| WO | WO 2008/036967 | 3/2008 |
| WO | WO 2008/151211 | 12/2008 |
| WO | WO 2010/001220 | 1/2010 |
| WO | WO 2012/065953 | 5/2012 |
| WO | WO 2012/116415 | 9/2012 |
| WO | WO 2014/083033 | 6/2014 |
| WO | WO 2014/198849 | 12/2014 |
| WO | WO 2018/172423 | 9/2018 |
| WO | WO 2020/069008 | 4/2020 |

OTHER PUBLICATIONS

Kany et al., "Binding Mode Characterization and Early in Vivo Evaluation of Fragment-Like Thiols as Inhibitors of the Virulence Factor LasB from *Pseudomonas aeruginosa*," *ACS Infectious Diseases*, 4:988-997, 2018.
Liu et al., "The modified-Mannich reaction: Conversion of arylboronic acids and subsequent coupling with paraformaldehyde and amines toward the one-pot synthesis of Mannich bases and benzoaxazines," *Tetrahedron Letters* 58:1470-1473, 2017.
Malinger et al., "Discovery of Potent, Selective, and Orally Bioavailable Small-Molecule Modulators of the Mediator Complex-Associated Kinases CDK8 and CDK19," *Journal of Medicinal Chemistry* 59:1078-1101, 2016.
Robinson et al., "Inhibitors of MMP-1: An Examination of $P_1{}^1C_\alpha$ Gem-Disubstitution in the Succinamide Hydroxamate Series," *Bioorganic & Medicinal Chemistry Letters* 6(14):1719-1724, 1996.
Seth, "A Comprehensive Review on Recent Advances in Synthesis & Pharmacotherapeutic Potential of Benzothiazoles," *Anti-Inflammatory & Anti-Allergy Agents in Medicinal Chemistry* 14:98-112, 2015.
Takagi et al., "Palladium(0)-catalyzed Synthesis of 2-Alkylbenzothiazoles by a Novel Thiation of 1-Amino-2-iodoarenes with Thioamides," *Chemistry Letters* 116:839-840, 1987.
Valeur et al., "Amide bond formulation: beyond the myth of coupling reagents," *Chem. Soc. Rev.*, 28:606-631, 2009.
Yerdelen et al., "Synthesis of donepezil-based multifunctional agents for the treatment of Alzheimer's disease," *Bioorganic & Medicinal Chemistry Letters* 25:5576-5582, 2015.
Fei et al., "Recent progress of pseudomonas aeruginosa pneumonia" *Int. J. Respir.* 26(4):250-252, Apr. 2006 with English Translation.
Xin et al., "Pseudomonas aeruginosa biofilm infection," *JILIN Medical Journal* 36(7):1439-1442, 2015 with English Translation.

* cited by examiner

INDANE DERIVATIVES FOR USE IN THE TREATMENT OF BACTERIAL INFECTION

CROSS REFERENCE TO RELATED APPLICATIONS

This is the U.S. National Stage of International Application No. PCT/EP2019/070115, filed on Jul. 25, 2019, which in turn claims the benefit of Application Nos. EP18290106.6 filed on Sep. 25, 2018, EP18290104.1, filed on Sep. 26, 2018 and EP18197365.2 filed on Sep. 27, 2018. These applications are incorporated herein in their entireties.

FIELD OF THE INVENTION

The present invention relates to compounds which find use in the prevention or treatment of bacterial infection. The invention also provides such compounds per se and pharmaceutical compositions comprising such compounds.

BACKGROUND

Cystic fibrosis (CF) is a life-threatening disease affecting approximately 70,000 sufferers worldwide. CF is the most common lethal, hereditary disease in Caucasian populations, resulting from mutations in the cystic fibrosis transmembrane conductance regulator (CFTR) gene. The prevalence of CF in Europe is 1 in every 2,000-3,000 live births, and in North America is about 1 in every 3,500 births. In the UK there are approximately 9,800 people with CF.

The organs of individuals with CF typically have significantly thickened secretions. This in turn can lead to a range of pathological problems. For instance, individuals with CF typically have impaired ciliary clearance, and the lungs of such individuals are typically colonized and infected by bacteria from an early age. Such bacteria include *Staphylococcus aureus, Haemophilus influenza, Pseudomonas aeruginosa* and *Burkholderia cepacia. Pseudomonas aeruginosa* (PA) is the most common cause of chronic lung infection in individuals with CF, and chronic infection with PA is found in 9% of pre-school children, 32% of 10-15 year olds and the majority (between 59% and 80%) of adults with CF, leading to progressive lung damage and early death.

As the lung of the individual with CF is colonised by PA, the growth pattern of the bacteria changes and its capacity for survival improves. In chronic infection, PA bacteria on mucosal and epithelial surfaces, or in sputum, form biofilms as well as producing large quantities of alginate (the so-called mucoid phenotype) which reduce the effectiveness of phagocytosis and antibiotic therapy. This leads to chronic colonisation of the lung by PA that is not cleared by conventional antibiotic therapy.

Antibiotics are a broad range of substances exhibiting anti-bacterial activity. A large number of antibiotic compounds are known and have been shown to exhibit antibacterial activity against a wide range of bacteria. However, currently available antibiotics are incapable of controlling some bacterial infections. This is because the target bacteria have acquired antibiotic resistance, for example via horizontal gene transfer or because the target bacteria are found in a state in which the efficacy of antibiotics which would otherwise be highly active is reduced. One such state is a bacterial biofilm.

Bacteria in biofilms are enclosed in a self-produced extracellular biopolymer matrix, which may include polysaccharides, proteins and DNA. Bacteria in biofilms typically exhibit different properties from free-living bacteria of the same species. Such properties typically include increased resistance to antibiotics and detergents and increased lateral gene transfer. For example, bacteria in biofilms typically display up to 1,000-fold higher tolerance to antibiotic challenge than their single cell, planktonic (free-living) counterparts.

This limitation in the efficacy of antibacterial compounds is especially important for individuals who through immunodeficiency or other diseases or conditions cannot adequately combat bacterial infection. Such individuals include those suffering from cystic fibrosis.

CF patients who are colonised with PA show also a more rapid decline in lung function, faster decline in chest radiograph score, poor weight gain, increased hospitalisation rates and an increased need for antibiotic therapy. Median survival is reduced and mortality increased (2.6× risk of death). Most disease-related morbidity and mortality in CF is caused by progressive lung disease as a result of bacterial infection and airway inflammation, primarily associated with the effects of chronic PA lung infection and the persistence of PA biofilms.

Despite intensive antibiotic treatment, adaptive mechanisms such as biofilm formation allow PA to resist both immune and antibiotic pressures, leading to recurrent exacerbations and respiratory failure.

Pathogenic bacteria such as PA are not only of importance in the context of CF. For example, the opportunistic pathogen PA can also cause septic shock, particularly in neutropenic patients, and can be responsible for infections of the respiratory tract, the urinary tract, the gastrointestinal network and skin and soft tissues. PA is also a frequent coloniser of medical devices such as catheters, nebulizers, and the like.

Accordingly, there is a clear need for new antibiotic compounds and compositions and adjuvant therapies for treating bacterial infection.

SUMMARY OF THE INVENTION

The inventors have surprisingly found that compounds of Formula (I) are potent inhibitors of the *Pseudomonas aeruginosa*-derived elastase enzyme LasB, which is important in *Pseudomonas aeruginosa* pathogenesis and persistence through biofilm formation.

LasB is implicated in bacterial disease pathology, since secreted LasB degrades many host immune proteins and causes tissue damage. LasB, also known as pseudolysin, is massively secreted into the environment of the producer organism where it is able to proteolytically attack numerous host immune proteins (e.g. immunoglobulins, cytokines, SP-A, antimicrobial peptides (e.g. Trappin 2)) and tissue proteins (e.g. elastin). There are no mammalian homologues of LasB. The ability of LasB to attack host proteins contributes to immune evasion (e.g. avoidance of SP-A mediated phagocytosis, and degradation of immunoglobulin, degradation of antimicrobial peptides (e.g. Trappin 2)) whilst promoting tissue invasion and long term colonization. Inhibition of LasB therefore better equips the host to deal with immune attack.

LasB also has an important internal role within the bacterial cell cleaving nucleoside diphosphate kinase (NDK) to a smaller active form. Active form of NDK leads to increased GTP levels within the cell, increasing production of alginate. Alginate is a polysaccharide which is a major component of the extracellular biofilm matrix and which is required for swarming motility. Those two virulence phenotypes are associated with bacterial persistence in response to immune and antibiotic pressures. LasB activity has also been shown to upregulate rhamnolipid production, which is necessary for biofilm formation/maturation. Accordingly, inhibition of LasB assists impairment of biofilm formation and disruption of the established biofilm. This in turn is believed to better enable antibiotics currently in use to deal effectively with infection.

In addition, LasB directly activates interleukin-1-β (IL-1β). IL-1β is a human protein and key initiator of inflammatory response. This proinflammatory cytokine is a clinical biomarker of inflammation and is upregulated during acute pulmonary exacerbations in CF patients. IL-1β is produced as an inactive form (pro-IL-1β) by host cells in response to pathogen detection and is activated via hydrolytic removal of a peptide moiety by the host caspase-1. Recent research has demonstrated that the *Pseudomonas aeruginosa* (PA)-secreted elastase LasB can also cleave and activate IL-1β. This activation is through a cleavage at an alternative and distinct site from caspase-1. Because LasB directly activates IL-1β by hydrolysis of pro-IL-1β, IL-1β can be thus considered as a marker for PA LasB activity both in vitro and in vivo. The inventors have recognised that the ability of LasB to activate IL-1β leads to applications of inhibitors of LasB in treating inflammation and related conditions.

Accordingly, the present invention provides the following aspects:

1. A compound which is an indane according to Formula (I), or a pharmaceutically acceptable salt thereof,

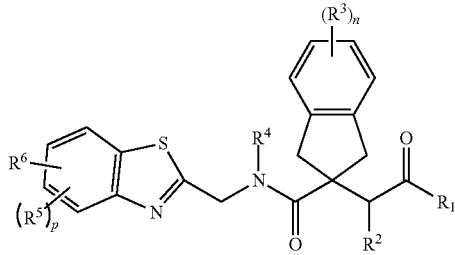

[FORMULA (I)]

wherein
R$^1$ is selected from:
NHOH, —OH, —OR$^{1a}$ and —OCH$_2$OC(O)R$^{1a}$, wherein R$^{1a}$ is selected from an unsubstituted C$_1$ to C$_4$ alkyl group and phenyl; and
where the compound of Formula (I) contains a positively charged nitrogen atom, R$^1$ may be O$^-$, such that the compound forms a zwitterion;
R$^2$ is selected from H and unsubstituted C$_1$ to C$_2$ alkyl;
each R$^3$ group is independently selected from halogen, —OH, —NH$_2$, methyl and —CF$_3$;
n is an integer from 0 to 4;
R$^4$ is selected from H and unsubstituted C$_1$ to C$_2$ alkyl;
R$^6$ is C$_2$ to C$_4$ alkoxy which is unsubstituted or is substituted with a group selected from —OH; —NR$^{10}$R$^{11}$; —N$^+$R$^{10}$R$^{11}$R$^{12}$; —OR$^{6a}$ and —NR$^{10}$R$^{6a}$, wherein R$^{6a}$ is a C$_1$ to C$_3$ alkyl group which is unsubstituted or substituted with a group selected from OH; —NR$^{10}$R$^{11}$; —N$^+$R$^{10}$R$^{11}$R$^{12}$; —NR$^{10}$NR$^{11}$R$^{12}$; —NR$^{10}$N$^+$R$^{11}$R$^{12}$R$^{13}$; —N$^+$R$^{10}$R$^{11}$NR$^{12}$R$^{13}$; —NR$^{10}$C(NR$^{11}$)NR$^{12}$R$^{13}$; —NR$^{10}$C(N$^+$R$^{11}$R$^{12}$)NR$^{13}$R$^{14}$; —C(NR$^{10}$)NR$^{11}$R$^{12}$; and —C(N$^+$R$^{10}$R$^{11}$)NR$^{12}$R$^{13}$;

p is 0 or 1;
R$^5$ is selected from —OMe, —OH, halogen, —NR$_{10}$R$^{11}$; —N$^+$R$^{10}$R$^{11}$R$^{12}$, —CF$_3$; and
R$^{10}$, R$^{11}$, R$^{12}$R$^{13}$ and R$^{14}$ are independently H or methyl;
with the proviso that the indane of Formula (I) is other than:
2-(2-(((4-ethoxybenzo[d]thiazol-2-yl)methyl)carbamoyl)-2,3-dihydro-1H-inden-2-yl)acetic acid;
2-[2-[(6-ethoxy-1,3-benzothiazol-2-yl)methylcarbamoyl]indan-2-yl]acetic acid;
2-[2-[[6-(2-hydroxyethoxy)-1,3-benzothiazol-2-yl]methylcarbamoyl]indan-2-yl]acetic acid;
2-[2-[[6-[2-(dimethylamino)ethoxy]-1,3-benzothiazol-2-yl]methylcarbamoyl]indan-2-yl]acetic acid;
2-[2-[[6-[2-(trimethylammonio)ethoxy]-1,3-benzothiazol-2-yl]methylcarbamoyl]indan-2-yl]acetate;
2-[2-[[5-[2-(dimethylamino)ethoxy]-1,3-benzothiazol-2-yl]methylcarbamoyl]indan-2-yl]acetic acid;
2-[2-[[5-[2-(trimethylammonio)ethoxy]-1,3-benzothiazol-2-yl]methylcarbamoyl]indan-2-yl]acetate;
2-(2-(((5-(3-(dimethylamino)propoxy)-6-methoxybenzo[d]thiazol-2-yl)methyl)carbamoyl)-5,6-difluoro-2,3-dihydro-1H-inden-2-yl)acetic acid;
2-(5,6-difluoro-2-(((6-methoxy-5-(3-(trimethylammonio)propoxy)benzo[d]thiazol-2-yl)methyl)carbamoyl)-2,3-dihydro-1H-inden-2-yl)acetate; and
2-(2-(((5-(2-(dimethylamino)ethoxy)-6-methoxybenzo[d]thiazol-2-yl)methyl)carbamoyl)-2,3-dihydro-1H-inden-2-yl)acetic acid.

2. A compound according to aspect 1, wherein R$^1$ is selected from —OH and —NHOH, or where the compound of Formula (I) contains a positively charged nitrogen atom, R$^1$ may be O$^-$, such that the compound forms a zwitterion.

3. A compound according to aspect 1 or aspect 2, wherein R$^2$ is H.

4. A compound according to aspect 1 or aspect 2, wherein R$^4$ is H.

5. A compound according to any one of the preceding aspects, wherein n is an integer from 0 to 2 and each R$^3$ group is halogen, preferably fluorine.

6. A compound according to any one of the preceding aspects, wherein R$^5$ is methoxy.

7. A compound according to any one of the preceding aspects, wherein R$^6$ is C$_2$ to C$_4$ alkoxy which is unsubstituted or is substituted with a group selected from —OH; —NR$^{10}$R$^{11}$; —N$^+$R$^{10}$R$^{11}$R$^{12}$; and —OR$^{6a}$, wherein R$^{6a}$ is a C$_1$ to C$_3$ alkyl group which is unsubstituted or substituted with a group selected from OH; —NR$^{10}$R$^{11}$; and —N$^+$R$^{10}$R$^{11}$R$^{12}$.

8. A compound according to any one of the preceding aspects, wherein p is 1; and R$^6$ is C$_2$ to C$_4$ alkoxy which is substituted with a group selected from —NMe$_2$; —N$^+$(Me)$_3$; and —OR$^{6a}$, wherein R$^{6a}$ is a C$_1$ to C$_3$ alkyl group which is unsubstituted or substituted with a group selected from —NR$^{10}$R$^{11}$; and —N$^+$R$^{10}$R$^{11}$R$^{12}$.

9. A compound according to any one of aspects 1 to 6, wherein R$^6$ is C$_2$ to C$_4$ alkoxy which is substituted with a group selected from —OR$^{6a}$ and —NR$^{10}$R$^{6a}$, wherein R$^{6a}$ is a C$_1$ to C$_3$ alkyl group which is unsubstituted or substituted with a group selected from OH; —NR$^{10}$R$^{11}$; —N$^+$R$^{10}$R$^{11}$R$^{12}$; —NR$^{10}$NR$^{11}$R$^{12}$; —NR$^{10}$N$^+$R$^{11}$R$^{12}$R$^{13}$; —N$^+$R$^{10}$R$^{11}$NR$^{12}$R$^{13}$; —NR$^{10}$C(NR$^{11}$)NR$^{12}$R$^{13}$; —NR$^{10}$C(N$^+$R$^{11}$R$^{12}$)NR$^{13}$R$^{14}$; —C(NR$^{10}$)NR$^{11}$R$^{12}$; and —C(N$^+$R$^{10}$R$^{11}$)NR$^{12}$R$^{13}$.

10. A compound according to any one of aspects 1 to 6, wherein R$^6$ is C$_2$ to C$_4$ alkoxy which is substituted with a group —OR$^{6a}$, wherein R$^h$a is a C$_1$ to C$_3$ alkyl group which is unsubstituted or substituted with a group selected from OH; —NR$^{10}$R$^{11}$; and —N$^+$R$^{10}$R$^{11}$R$^{12}$.

11. A compound according to aspect 1 which is 2-[5,6-difluoro-2-[[6-methoxy-5-[2-[2-(trimethylammonio)ethoxy]ethoxy]-1,3-benzothiazol-2-yl]methylcarbamoyl]indan-2-yl]acetate or a pharmaceutically acceptable salt thereof.

12. A compound according to aspect 1 which is 2-[2-[[6-methoxy-5-[3-(trimethylammonio)propoxy]-1,3-benzothiazol-2-yl]methylcarbamoyl]indan-2-yl]acetate or a pharmaceutically acceptable salt thereof.

13. A compound according to aspect 1 which is 2-[2-[[6-methoxy-5-[2-[2-(trimethylammonio)ethoxy]ethoxy]-1,3-benzothiazol-2-yl]methylcarbamoyl]indan-2-yl]acetate or a pharmaceutically acceptable salt thereof.

14. A compound according to aspect 1 which is
2-[2-[[6-(3-hydroxypropoxy)-1,3-benzothiazol-2-yl]methylcarbamoyl]indan-2-yl]acetic acid;
2-[2-[(6-propoxy-1,3-benzothiazol-2-yl)methylcarbamoyl]indan-2-yl]acetic acid;
2-[2-[[5-[3-(dimethylamino)propoxy]-6-methoxy-1,3-benzothiazol-2-yl]methylcarbamoyl]indan-2-yl]acetic acid;
2-[5,6-difluoro-2-[[6-methoxy-5-[2-(trimethylammonio)ethoxy]-1,3-benzothiazol-2-yl]methylcarbamoyl]indan-2-yl]acetate;
2-(2-(((5-(4-(dimethylamino)butoxy)-6-methoxybenzo[d]thiazol-2-yl)methyl)carbamoyl)-2,3-dihydro-1H-inden-2-yl)acetic acid;
2-(2-(((6-methoxy-5-(4-(trimethylammonio)butoxy)benzo[d]thiazol-2-yl)methyl)carbamoyl)-2,3-dihydro-1H-inden-2-yl)acetate;
or a pharmaceutically acceptable salt thereof.

15. A pharmaceutical composition comprising (i) a compound according to any one of the preceding aspects and (ii) at least one pharmaceutically acceptable carrier or diluent; and optionally further comprising (iii) an antibiotic agent; wherein preferably the antibiotic agent is selected from tobramycin, neomycin, streptomycin, gentamycin, ceftazidime, ticarcillin, piperacillin, tazobactam, imipenem, meropenem, rifampicin, ciprofloxacin, amikacin, colistin, aztreonam, azithromycin and levofloxacin.

16. A combination of (i) a compound according to any one of aspects 1 to 14 and (ii) an antibiotic agent; wherein preferably the antibiotic agent is selected from tobramycin, neomycin, streptomycin, gentamycin, ceftazidime, ticarcillin, piperacillin, tazobactam, imipenem, meropenem, rifampicin, ciprofloxacin, amikacin, colistin, aztreonam, azithromycin and levofloxacin.

17. A compound according to any one of aspects 1 to 14; a composition according to aspect 15 or a combination according to aspect 16 for use in medicine.

18. A compound according to any one of aspects 1 to 14; a composition according to aspect 15 or a combination according to aspect 16 for use in treating or preventing bacterial infection in a subject.

19. A compound for use, composition for use or combination for use according to aspect 18 wherein the bacterial infection is caused by *Bacillus, Pseudomonas, Staphylococcus, Streptococcus, Listeria, Burkholderia* or *Escherichia*.

20. A compound for use, composition for use or combination for use according to aspect 18 or 19 which is for use in the treatment or prevention of pneumonia.

21. A compound according to any one of aspects 1 to 14; a composition according to aspect 15 or a combination according to aspect 16 for use in treating or preventing inflammation in a subject.

22. A compound for use, composition for use or combination for use according to aspect 21 which is for use in the treatment or prevention of respiratory tract inflammation in a subject.

23. A compound for use, composition for use or combination for use according to aspect 21 or aspect 22 wherein the inflammation is caused by a bacterial infection.

24. A compound for use, composition for use or combination for use according to any one of aspects 18 to 23 wherein the subject suffers from cystic fibrosis.

25. A compound for use, composition for use or combination for use according to any one of aspects 18 to 24 wherein the subject suffers from chronic obstructive pulmonary disease (COPD), bronchiectasis, and/or ventilator-associated pneumonia (VAP).

DETAILED DESCRIPTION OF THE INVENTION

Definitions

Figure 1:
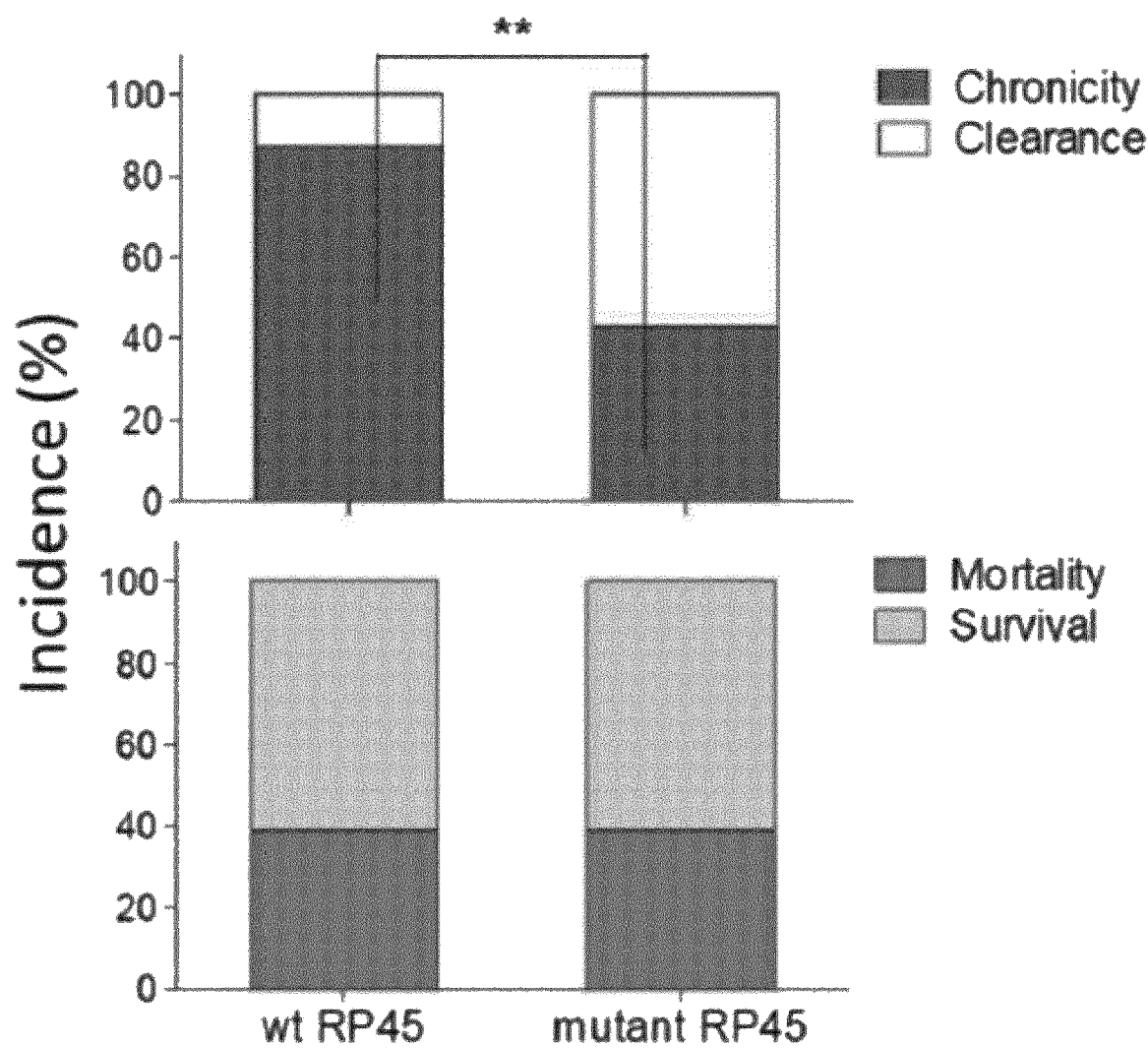
FIG. 1 shows incidences of mortality vs survival and chronic colonization vs bacterial clearance in a mouse model of lung infection, 7 days post-infection with wt and ΔlasB mutant PA strains. Results are discussed in Example 8.
**p<0.01.

As used herein, a $C_1$ to $C_4$ alkyl group is a linear or branched alkyl group containing from 1 to 4 carbon atoms. A $C_1$ to $C_4$ alkyl group is often a $C_1$ to $C_3$ alkyl group. Examples of $C_1$ to $C_4$ alkyl groups include methyl, ethyl, n-propyl, iso-propyl, n-butyl, sec-butyl, and tert-butyl. A $C_1$ to $C_3$ alkyl group is typically a $C_1$ to $C_2$ alkyl group. A $C_1$ to $C_2$ alkyl group is methyl or ethyl, typically methyl. For the avoidance of doubt, where two alkyl groups are present, the alkyl groups may be the same or different.

As used herein, an alkoxy group is typically a said alkyl group attached to an oxygen atom. Thus, a $C_2$ to $C_4$ alkoxy group is a $C_2$ to $C_4$ alkyl group attached to an oxygen atom. A $C_1$ to $C_3$ alkoxy group is a $C_1$ to $C_3$ alkyl group attached to an oxygen atom. Examples of $C_2$ to $C_4$ alkoxy groups include ethoxy, n-propyoxy, iso-propoxy, n-butoxy, sec-butoxy, and tert-butoxy. Examples of $C_1$ to $C_3$ alkoxy groups include methoxy, ethoxy n-propyoxy and iso-propoxy. Typically, a $C_1$ to $C_3$ alkoxy group is a $C_1$ to $C_2$ alkoxy group such as a methoxy or ethoxy group. For the avoidance of doubt, where two alkoxy groups are present, the alkoxy groups may be the same or different.

As used herein, a halogen is typically chlorine, fluorine, bromine or iodine and is preferably chlorine, bromine or fluorine, especially chorine or fluorine.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as oxalic, citric, fumaric, maleic, malic, ascorbic, succinic, tartaric, palmitic, benzoic, acetic, triphenylacetic, methanesulphonic, ethanesulphonic, 1-hydroxy-2-naphthenoic, isethionic, benzenesulphonic or p-toluenesulphonic acid. Pharmaceutically acceptable bases include alkali metal (e.g. sodium or potassium), alkali earth metal (e.g. calcium or magnesium) and zinc bases, for example hydroxides, carbonates, and bicarbonates, and organic bases such as alkyl amines, aralkyl (i.e. aryl-substituted alkyl; e.g. benzyl) amines and heterocyclic amines.

Where the compound of Formula (I) contains a positively charged nitrogen atom, the compound may exist as a zwitterion, where $R^1$ is $O^-$, thus leaving a $COO^-$ group. Such compounds may also be provided in the form of a pharmaceutically acceptable salt. Suitable salts include those formed with pharmaceutically acceptable acids, which provide a proton to the $COO^-$ group, and a counter-ion to balance the positive charge on the quaternary nitrogen atom. Suitable pharmaceutically acceptable acids include hydrochloric acid, sulphonic acids including methanesulphonic acid and toluene sulphonic acid, ascorbic acid and citric acid. Hydrochloric acid and sulphonic acids are preferred, in particular hydrochloric acid. Alternatively, zwitterions can be combined with pharmaceutically acceptable bases as mentioned above, for example, alkali metal (e.g. sodium or potassium) and alkali earth metal (e.g. calcium or magnesium) hydroxides.

In Formula (I), the stereochemistry is not limited. In particular, compounds of Formula (I) containing one or more stereocentre (e.g. one or more chiral centre) may be used in enantiomerically or diastereoisomerically pure form, or in the form of a mixture of isomers. Further, for the avoidance of doubt, the compounds of the invention may be used in any tautomeric form. Typically, the agent or substance described herein contains at least 50%, preferably at least 60, 75%, 90% or 95% of a compound according to Formula (I) which is enantiomerically or diastereomerically pure. Thus, the compound is preferably substantially optically pure.

For the avoidance of doubt, the terms 'indanyl derivative' and 'indane derivative' may be used interchangeably and unless otherwise indicated refer to compounds of the invention, such as compounds of Formula (I).

Compounds of the Invention

Typically, $R^1$ is selected from OH, NHOH and $OR^{1a}$, e.g. from OH and $OR^{1a}$, or where the compound of Formula (I) contains a positively charged nitrogen atom, $R^1$ may be $O^-$, such that the compound forms a zwitterion. $R^{1a}$ is typically an unsubstituted $C_1$ to $C_4$ alkyl group, such as an unsubstituted $C_1$ to $C_2$ alkyl group. More preferably, $R^{1a}$ is methyl or t-butyl.

More preferably, $R^1$ is OH or NHOH, or where the compound of Formula (I) contains a positively charged nitrogen atom, $R^1$ may be $O^-$, such that the compound forms a zwitterion. Still more preferably, $R^1$ is OH, or where the compound of Formula (I) contains a positively charged nitrogen atom, $R^1$ may be $O^-$, such that the compound forms a zwitterion.

Typically, $R^2$ is selected from H and methyl. Most preferably, $R^2$ is H. $R^4$ is typically H or methyl. Preferably, $R^4$ is H. Most preferably, $R^2$ and $R^4$ are independently H or methyl, most preferably they are both H.

Each $R^3$ group is typically independently selected from halogen; and —OH; and —$NH_2$. More preferably, each $R^3$ group is independently selected from halogen (e.g. fluorine or chlorine) and —OH. Yet more preferably each $R^3$ group is halogen, most preferably fluorine. Typically, n is an integer from 0 to 2; more preferably n is 0 or 1; most preferably n is 0.

Preferably, where more than one $R^3$ group is present, each $R^3$ is the same. For example, in some preferred compounds, n is 0; or n is 1 or 2 and each $R^3$ is independently selected from a halogen and —OH. In some more preferred compounds, n is 0; or n is 1 or 2, preferably 2, and each $R^3$ is independently a halogen, preferably fluorine.

Preferably, in Formula (I), $R^1$ is selected from OH and NHOH, or where the compound of Formula (I) contains a positively charged nitrogen atom, $R^1$ may be $O^-$, such that a $COO^-$ group is present and the compound forms a zwitterion; $R^2$ is selected from H and methyl; each $R^3$ group is independently selected from halogen (e.g. fluorine or chlorine); and —OH; n is an integer from 0 to 2, and $R^4$ is H.

More preferably, in Formula (I), $R^1$ is OH, or where the compound of Formula (I) contains a positively charged nitrogen atom, $R^1$ may be $O^-$, such that a $COO^-$ group is present and the compound forms a zwitterion; $R^2$ is H; each $R^3$ group is independently selected from halogen, preferably fluorine; n is an integer from 0 to 2, and $R^4$ is H.

$R^5$ is preferably methoxy.

p is 0 or 1, preferably 1.

In some preferred compounds, therefore, $R^1$ is OH, or where the compound of Formula (I) contains a positively charged nitrogen atom, $R^1$ may be $O^-$, such that a $COO^-$ group is present and the compound forms a zwitterion; n is 0; or n is 1 or 2, preferably 2, and each $R^3$ is independently a halogen, preferably fluorine; p is 0 or 1 and $R^5$ if present is methoxy.

$R^6$ is $C_2$ to $C_4$ alkoxy, for example ethoxy, n-propoxy or n-butoxy, preferably ethoxy or n-propoxy, each of which may be unsubstituted or substituted.

Typically, $R^6$ is unsubstituted or is substituted with a group selected from —OH; —$NR^{10}R^{11}$; —$N^+R^{10}R^{11}R^{12}$; and —$OR^{6a}$. In one embodiment, $R^6$ is $C_2$ to $C_4$ alkoxy which is substituted with a group selected from —OH; —$NR_{10}R^{11}$; —$N^+R^{10}R^{11}R^{12}$; —$OR^{6a}$ and —$NR^{10}R^{6a}$. Preferably, $R^6$ is $C_2$ to $C_4$ alkoxy which is substituted with a group selected from —OH; —$NR^{10}R^{11}$; —$N^+R^{10}R^{11}$; —$N^+R^{10}R^{11}R^{12}$; and —$OR^{6a}$. Most preferably, $R^6$ is $C_2$ to $C_4$ alkoxy which is substituted with a group selected from —$NR^{10}R^{11}$; —$N^+R^{10}R^{11}R^{12}$; and —$OR^{6a}$. Most preferably, $R^6$ is $C_2$ to $C_4$ alkoxy which is substituted with a group —$OR^{6a}$.

In some preferred compounds, $R^{6a}$ is a $C_1$ alkyl group which is unsubstituted or substituted with a group selected from OH; —$NR_{10}R^{11}$; —$N^+R^{10}R^{11}R^{12}$; —$NR^{10}NR^{11}R^{12}$; —$NR^{10}N^+R^{11}R^{12}R^{13}$; —$N^+R^{10}R^{11}NR^{12}R^{13}$; —$NR^{10}C(NR^{11})NR^{12}R^{13}$; —$NR^{10}C(N^+R^{11}R^{12})NR^{13}R^{14}$; —$C(NR^{10})NR^{11}R^{12}$; and —$C(N^+R^{10}R^{11})NR^{12}R^{13}$; or is a $C_2$ to $C_3$ alkyl group which is substituted with a group selected from —$NR_{10}R^{11}$; —$N^+R^{10}R^{11}R^{12}$; —$NR^{10}NR^{11}R^{12}$; —$NR^{10}N^+R^{11}R^{12}R^{13}$; —$N^+R^{10}R^{11}NR^{12}R^{13}$; —$NR^{10}C(NR^{11})NR^{12}R^{13}$; —$NR^{10}C(N^+R^{11}R^{12})NR^{13}R^{14}$; —$C(NR^{10})NR^{11}R^{12}$; and —$C(N^+R^{10}R^{11})NR^{12}R^{13}$. In other preferred compounds $R^{6a}$ is a $C_1$ to $C_3$ alkyl group which is substituted with a group selected from —$NR_{10}R^{11}$; —$N^+R^{10}R^{11}R^{12}$; —$NR^{10}NR^{11}R^{12}$; —$NR^{10}N^+R^{11}R^{12}R^{13}$; —$N^+R^{10}R^{11}NR^{12}R^{13}$; —$NR^{10}C(NR^{11})NR^{12}R^{13}$; —$NR^{10}C(N^+R^{11}R^{12})NR^{13}R^{14}$; —$C(NR^{10})NR^{11}R^{12}$; and —$C(N^+R^{10}R^{11})NR^{12}R^{13}$.

$R^{6a}$ is typically a $C_1$ to $C_3$ alkyl group which is unsubstituted or substituted with a group selected from OH; —$NR^{10}R^{11}$; and —$N^+R^{10}R^{11}R^{12}$. Preferably, $R^{6a}$ is a $C_1$ to $C_3$ alkyl group which is unsubstituted or substituted with a group selected from OH; —$NMe_2$; and —$N^+Me_3$. More preferably, $R^{6a}$ is a $C_1$ to $C_2$ alkyl group which is unsubstituted or substituted with a group selected from OH; —$NMe_2$; and —$N^+Me_3$.

Thus, $R^6$ is preferably $C_2$ to $C_4$ alkoxy which is unsubstituted or is substituted with a group selected from —OH; —$NR^{10}R^{11}$; —$N^+R^{10}R^{11}R^{12}$; and —$OR^{6a}$, wherein $R^{6a}$ is a $C_1$ to $C_3$ alkyl group which is unsubstituted or substituted with a group selected from OH; —$NR^{10}R^{11}$; and —$N^+R^{10}R^{11}R^{12}$. More preferably, $R^6$ is $C_2$ to $C_4$ alkoxy which is unsubstituted or is substituted with a group selected from —OH; —$NMe_2$; —$N^+Me_3$; and —$OR^{6a}$, wherein $R^{6a}$ is a $C_1$ to $C_3$ alkyl group which is unsubstituted or substituted with a group selected from —$NMe_2$; and —$N^+(Me)_3$. Preferably, $R^6$ is $C_2$ to $C_4$ alkoxy which is unsubstituted or is substituted with a group selected from —OH; —$NMe_2$; —$N^+(Me)_3$; and —$OR^{6a}$, wherein $R^h a$ is a $C_1$ to $C_2$ alkyl group which is substituted with a group selected from —$NMe_2$; and —$N^+(Me)_3$. Most preferably, $R^6$ is $C_2$ to $C_4$ alkoxy which is unsubstituted or is substituted with a group selected from —OH; —$NMe_2$; —$N^+(Me)_3$; —$O(CH_2)$—$NMe_2$; and —$O(CH_2)$—$N^+(Me)_3$.

Typically, $R^6$ is bonded at the ring position marked as 1 below. If a group $R^5$ is present, this is typically present at the position marked as 2 below.

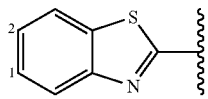 [SMILES: *c1nc2ccccc2s1]

Thus, the indane of Formula (I) is typically an indane of Formula (IA):

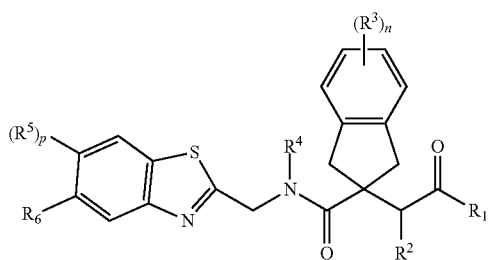

[FORMULA (IA)]

wherein $R^1$, $R^2$, $R^3$, $R^4$, $R^5$, $R^6$, n and p are as defined above.

Accordingly, preferred compounds of the invention are indanes of Formula (I) or Formula (IA) and pharmaceutically acceptable salts thereof wherein:

$R^1$ is selected from OH, NHOH and $OR^{1a}$, or where the compound of Formula (I) contains a positively charged nitrogen atom, $R^1$ may be $O^-$, such that a $COO^-$ group is present and the compound forms a zwitterion;

$R^2$ is selected from H and methyl;

each $R^3$ group is independently selected from halogen (e.g. fluorine or chlorine) and —OH;

n is an integer from 0 to 2;

$R^4$ is H;

$R^6$ is $C_2$ to $C_4$ alkoxy which is unsubstituted or is substituted with a group selected from —OH; —$NR^{10}R^{11}$; —$N^+R^{10}R^{11}R^{12}$; and —$OR^{6a}$, wherein $R^{6a}$ is a $C_1$ to $C_3$ alkyl group which is unsubstituted or substituted with a group selected from OH; —$NR^{10}R^{11}$; and —$N^+R^{10}R^{11}R^{12}$;

p is 0 or 1;

$R^5$ is methoxy; and $R^{10}$, $R^{11}$ and $R^{12}$ are independently H or methyl;

with the proviso that the indane of Formula (I) is other than:

2-(2-(((4-ethoxybenzo[d]thiazol-2-yl)methyl)carbamoyl)-2,3-dihydro-1H-inden-2-yl)acetic acid;

2-[2-[(6-ethoxy-1,3-benzothiazol-2-yl)methylcarbamoyl]indan-2-yl]acetic acid;

2-[2-[[6-(2-hydroxyethoxy)-1,3-benzothiazol-2-yl]methylcarbamoyl]indan-2-yl]acetic acid;

2-[2-[[6-[2-(dimethylamino)ethoxy]-1,3-benzothiazol-2-yl]methylcarbamoyl]indan-2-yl]acetic acid;

2-[2-[[6-[2-(trimethylammonio)ethoxy]-1,3-benzothiazol-2-yl]methylcarbamoyl]indan-2-yl]acetate;

2-[2-[[5-[2-(dimethylamino)ethoxy]-1,3-benzothiazol-2-yl]methylcarbamoyl]indan-2-yl]acetic acid;

2-[2-[[5-[2-(trimethylammonio)ethoxy]-1,3-benzothiazol-2-yl]methylcarbamoyl]indan-2-yl]acetate;

2-(2-(((5-(3-(dimethylamino)propoxy)-6-methoxybenzo[d]thiazol-2-yl)methyl)carbamoyl)-5,6-difluoro-2,3-dihydro-1H-inden-2-yl)acetic acid;

2-(5,6-difluoro-2-(((6-methoxy-5-(3-(trimethylammonio)propoxy)benzo[d]thiazol-2-yl)methyl)carbamoyl)-2,3-dihydro-1H-inden-2-yl)acetate; and 2-(2-(((5-(2-(dimethylamino)ethoxy)-6-methoxybenzo[d]thiazol-2-yl)methyl)carbamoyl)-2,3-dihydro-1H-inden-2-yl)acetic acid.

More preferred compounds of the invention are indanes of Formula (I) or Formula (IA) and pharmaceutically acceptable salts thereof wherein:

$R^1$ is OH, or where the compound of Formula (I) contains a positively charged nitrogen atom, $R^1$ may be $O^-$, such that a $COO^-$ group is present and the compound forms a zwitterion;

$R^2$ is H;

each $R^3$ group is independently selected from halogen, preferably fluorine;

n is an integer from 0 to 2;

$R^4$ is H;

$R^6$ is $C_2$ to $C_4$ alkoxy which is unsubstituted or is substituted with a group selected from —OH; —$NMe_2$; —$N^+Me_3$; and —$OR^{6a}$, wherein $R^{6a}$ is a $C_1$ to $C_3$ alkyl group which is unsubstituted or substituted with a group selected from —$NMe_2$; and —$N^+F(Me)_3$; most preferably $R^6$ is $C_2$ to $C_4$ alkoxy which is unsubstituted or substituted with a group selected from —OH; —$NMe_2$; —$N^+(Me)_3$; —$O(CH_2)$—$NMe_2$; and —$O(CH_2)$—$N^+(Me)_3$;

p is 0 or 1;

$R^5$ is methoxy; and $R^{10}$, $R^{11}$ and $R^{12}$ are independently H or methyl;

with the proviso that the indane of Formula (I) is other than:

2-(2-(((4-ethoxybenzo[d]thiazol-2-yl)methyl)carbamoyl)-2,3-dihydro-1H-inden-2-yl)acetic acid;

2-[2-[(6-ethoxy-1,3-benzothiazol-2-yl)methylcarbamoyl]indan-2-yl]acetic acid;

2-[2-[[6-(2-hydroxyethoxy)-1,3-benzothiazol-2-yl]methylcarbamoyl]indan-2-yl]acetic acid;

2-[2-[[6-[2-(dimethylamino)ethoxy]-1,3-benzothiazol-2-yl]
methylcarbamoyl]indan-2-yl]acetic acid;
2-[2-[[6-[2-(trimethylammonio)ethoxy]-1,3-benzothiazol-
2-yl]methylcarbamoyl]indan-2-yl]acetate;
2-[2-[[5-[2-(dimethylamino)ethoxy]-1,3-benzothiazol-2-yl]
methylcarbamoyl]indan-2-yl]acetic acid;
2-[2-[[5-[2-(trimethylammonio)ethoxy]-1,3-benzothiazol-
2-yl]methylcarbamoyl]indan-2-yl]acetate;
2-(2-(((5-(3-(dimethylamino)propoxy)-6-methoxybenzo[d]
thiazol-2-yl)methyl)carbamoyl)-5,6-difluoro-2,3-di-
hydro-1H-inden-2-yl)acetic acid;
2-(5,6-difluoro-2-(((6-methoxy-5-(3-(trimethylammonio)
propoxy)benzo[d]thiazol-2-yl)methyl)carbamoyl)-2,3-di-
hydro-1H-inden-2-yl)acetate; and
2-(2-(((5-(2-(dimethylamino)ethoxy)-6-methoxybenzo[d]
thiazol-2-yl)methyl)carbamoyl)-2,3-dihydro-1H-inden-2-
yl)acetic acid.

Further preferred compounds of the invention are indanes of Formula (I) or (IA) and pharmaceutically acceptable salts thereof, wherein
$R^1$, $R^2$, $R^3$, $R^4$, $R^5$ and n are as defined above;
p is 1; and
$R^6$ is $C_2$ to $C_4$ alkoxy which is substituted with a group selected from $-NR^{10}R^{11}$; $-N^+R^{10}R^{11}R^{12}$; and $-OR^{6a}$, wherein $R^{6a}$ is a $C_1$ to $C_3$ alkyl group which is unsubstituted or substituted with a group selected from $-NR^{10}R^{11}$; and $-N^+R^{10}R^{11}R^{12}$; and
with the proviso that the indane of Formula (I) is other than:
2-(2-(((5-(3-(dimethylamino)propoxy)-6-methoxybenzo[d]
thiazol-2-yl)methyl)carbamoyl)-5,6-difluoro-2,3-di-
hydro-1H-inden-2-yl)acetic acid;
2-(5,6-difluoro-2-(((6-methoxy-5-(3-(trimethylammonio)
propoxy)benzo[d]thiazol-2-yl)methyl)carbamoyl)-2,3-di-
hydro-1H-inden-2-yl)acetate; and
2-(2-(((5-(2-(dimethylamino)ethoxy)-6-methoxybenzo[d]
thiazol-2-yl)methyl)carbamoyl)-2,3-dihydro-1H-inden-2-
yl)acetic acid.

In this embodiment, $R^6$ is preferably $C_2$ to $C_4$ alkoxy which is substituted with a group selected from $-NMe_2$; $-N^+Me_3$; and $-OR^{6a}$, wherein $R^{6a}$ is a $C_1$ to $C_3$ alkyl group which is unsubstituted or substituted with a group selected from $-NMe_2$; and $-N^+(Me)_3$. Preferably, $R^6$ is $C_2$ to $C_4$ alkoxy which is substituted with a group selected from $-NMe_2$; $-N^+(Me)_3$; and $-OR^{6a}$, wherein $R^{6a}$ is a $C_1$ to $C_2$ alkyl group which is substituted with a group selected from $-NMe_2$; and $-N^+(Me)_3$. Most preferrably, $R^6$ is $C_2$ to $C_4$ alkoxy which is substituted with a group selected from $-NMe_2$; $-N^+(Me)_3$; $-O(CH_2)-NMe_2$; and $-O(CH_2)-N^+(Me)_3$.

Further preferred compounds of the invention are indanes of Formula (I) or (IA) and pharmaceutically acceptable salts thereof, wherein
$R^1$, $R^2$, $R^3$, $R^4$, $R^5$, n and p are as defined above; and
$R^6$ is $C_2$ to $C_4$ alkoxy which is substituted with a group selected from $-OR^{6a}$ and $-NR^{10}R^{6a}$, wherein $R^{6a}$ is a $C_1$ to $C_3$ alkyl group which is unsubstituted or substituted with a group selected from OH; $-NR^{10}R^{11}$; $-N^+R^{10}R^{11}R^{12}$; $-NR^{10}NR^{11}R^{12}$; $-NR^{10}N^+R^{11}R^{12}R^{13}$; $-N^+R^{10}R^{11}NR^{12}R^{13}$; $-NR^{10}C(NR^{11})NR^{12}R^{13}$; $-NR^{10}C(N^+R^{11}R^{12})NR^{13}R^{14}$; $-C(NR^{10})NR^{11}R^{12}$; and $-C(N^+R^{10}R^{11})NR^{12}R^{13}$.

Preferably in this embodiment $R^6$ is $C_2$ to $C_4$ alkoxy which is substituted with a group $-OR^{6a}$, wherein $R^{6a}$ is a $C_1$ to $C_3$ alkyl group which is unsubstituted or substituted with a group selected from OH; $-NR^{10}R^{11}$; and $-N^+R^{10}R^{11}R^{12}$. More preferably, $R^{6a}$ is a $C_1$ to $C_3$ alkyl group which is unsubstituted or substituted with a group selected from $-NMe_2$; and $-N^+(Me)_3$. More preferably, $R^{6a}$ is a $C_1$ to $C_2$ alkyl group which is substituted with a group selected from $-NMe_2$; and $-N^+(Me)_3$. Most preferrably, $R^{6a}$ is $-O(CH_2)-NMe_2$; or $-O(CH_2)-N^+(Me)_3$.

Preferred compounds of the invention are:
2-[2-[[6-(3-hydroxypropoxy)-1,3-benzothiazol-2-yl]meth-
ylcarbamoyl]indan-2-yl]acetic acid;
2-[2-[(6-propoxy-1,3-benzothiazol-2-yl)methylcarbamoyl]
indan-2-yl]acetic acid;
2-[2-[[5-[3-(dimethylamino)propoxy]-6-methoxy-1,3-ben-
zothiazol-2-yl]methylcarbamoyl]indan-2-yl]acetic acid;
2-[2-[[6-methoxy-5-[3-(trimethylammonio)propoxy]-1,3-
benzothiazol-2-yl]methylcarbamoyl]indan-2-yl]acetate;
2-[2-[[6-methoxy-5-[2-[2-(trimethylammonio)ethoxy]
ethoxy]-1,3-benzothiazol-2-yl]methylcarbamoyl]indan-
2-yl]acetate;
2-[5,6-difluoro-2-[[6-methoxy-5-[2-[2-(trimethylammonio)
ethoxy]ethoxy]-1,3-benzothiazol-2-yl]methylcarbamoyl]
indan-2-yl]acetate;
2-[5,6-difluoro-2-[[6-methoxy-5-[2-(trimethylammonio)
ethoxy]-1,3-benzothiazol-2-yl]methylcarbamoyl]indan-
2-yl]acetate;
2-(2-(((5-(4-(dimethylamino)butoxy)-6-methoxybenzo[d]
thiazol-2-yl)methyl)carbamoyl)-2,3-dihydro-1H-inden-2-
yl)acetic acid;
2-(2-(((6-methoxy-5-(4-(trimethylammonio)butoxy)benzo
[d]thiazol-2-yl)methyl)carbamoyl)-2,3-dihydro-1H-in-
den-2-yl)acetate; and
and pharmaceutically acceptable salts thereof.

Particularly preferred compounds of the invention are:
2-[2-[[6-(3-hydroxypropoxy)-1,3-benzothiazol-2-yl]meth-
ylcarbamoyl]indan-2-yl]acetic acid;
2-[2-[(6-propoxy-1,3-benzothiazol-2-yl)methylcarbamoyl]
indan-2-yl]acetic acid;
2-[2-[[5-[3-(dimethylamino)propoxy]-6-methoxy-1,3-ben-
zothiazol-2-yl]methylcarbamoyl]indan-2-yl]acetic acid;
2-[2-[[6-methoxy-5-[3-(trimethylammonio)propoxy]-1,3-
benzothiazol-2-yl]methylcarbamoyl]indan-2-yl]acetate;
2-[2-[[6-methoxy-5-[2-[2-(trimethylammonio)ethoxy]
ethoxy]-1,3-benzothiazol-2-yl]methylcarbamoyl]indan-
2-yl]acetate;
2-[5,6-difluoro-2-[[6-methoxy-5-[2-[2-(trimethylammonio)
ethoxy]ethoxy]-1,3-benzothiazol-2-yl]methylcarbamoyl]
indan-2-yl]acetate;
2-[5,6-difluoro-2-[[6-methoxy-5-[2-(trimethylammonio)
ethoxy]-1,3-benzothiazol-2-yl]methylcarbamoyl]indan-
2-yl]acetate; and
and pharmaceutically acceptable salts thereof.

Most preferred compounds are 2-[5,6-difluoro-2-[[6-methoxy-5-[2-[2-(trimethylammonio)ethoxy]ethoxy]-1,3-benzothiazol-2-yl]methylcarbamoyl]indan-2-yl]acetate;
2-[2-[[6-methoxy-5-[3-(trimethylammonio)propoxy]-1,3-benzothiazol-2-yl]methylcarbamoyl]indan-2-yl]acetate;
2-[2-[[6-methoxy-5-[2-[2-(trimethylammonio)ethoxy]ethoxy]-1,3-benzothiazol-2-yl]methylcarbamoyl]indan-2-yl]acetate and pharmaceutically acceptable salts of these compounds.

Synthesis

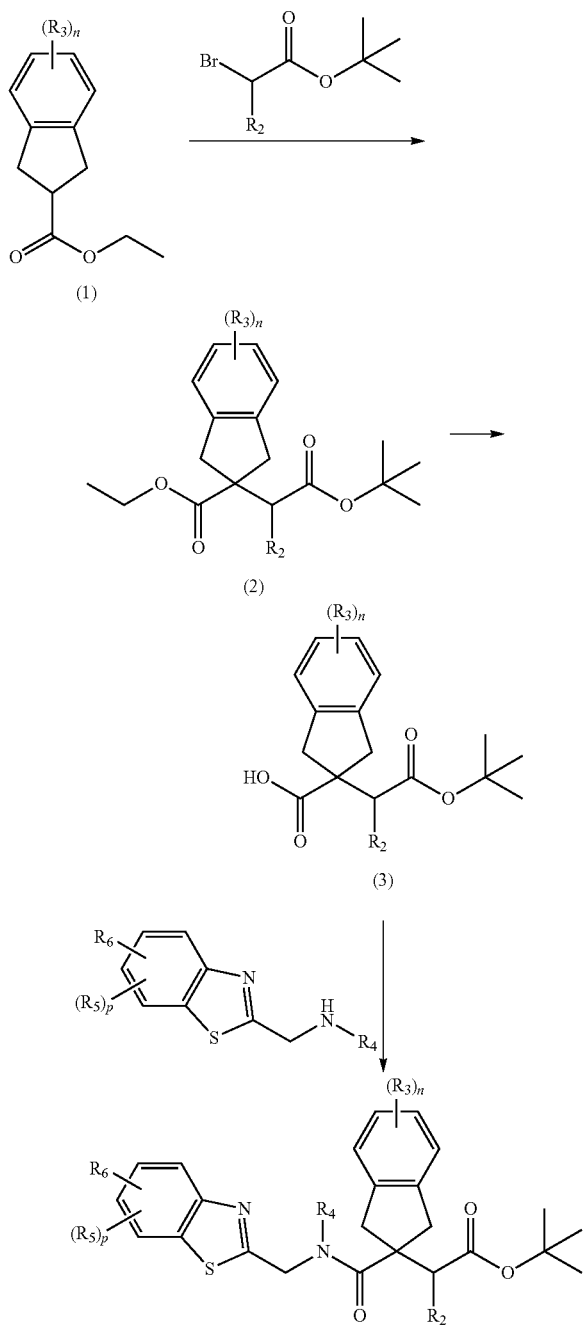

The compounds of the invention can be prepared by any suitable method. For example, as described in more detail below, deprotonation of commercially available ethyl esters (1) with strong base (such as sodium hexamethyldisilazide) then alkylation of the anion with tert-butyl bromoacetates gives diester (2) (Bell, I. M. and Stump, C. A., WO2006/29153; Robinson, R. P. et al, Bioorganic and Medicinal Chemistry Letters, 1996, 1719). Basic hydrolysis of the ethyl ester in the presence of the tert-butyl ester gives (3). Amide formation with a suitable 2-aminomethyl benzothiazole followed by treatment with TFA to remove the tert-butyl ester then affords the desired acids. Examples of suitable protocols for formation of amino-methyl benzothiazoles are provided below. The acids can be converted to esters ($R^1$=$OR^{1a}$) or other prodrug forms ($R^1$=$OCH_2OC(O)R^{1a}$) by techniques known to the skilled person.

There are numerous ways of accessing hydroxamic acids (for a review see Ganeshpurkar, A., et al, Current Organic Syntheses, 2018, 15, 154-165) but a very reliable procedure is to couple acids with O-(oxan-2-yl)hydroxylamine using peptide coupling conditions to give protected hydroxamates then deprotect with TFA to generate the hydroxamic acids (see for example Ding, C., et al, Bioorg. Med. Chem. Lett, 2017, 25, 27-37).

Compositions and Combinations

The present invention also provides a pharmaceutical composition, the pharmaceutical composition comprising a compound of the invention together with a pharmaceutically acceptable carrier or diluent. Typically, the composition contains up to 85 wt % of a compound of the invention. More typically, it contains up to 50 wt % of a compound of the invention. Preferred pharmaceutical compositions are sterile and pyrogen free. Further, when the pharmaceutical compositions provided by the invention contain a compound of the invention which is optically active, the compound of the invention is typically a substantially pure optical isomer.

The composition of the invention may be provided as a kit comprising instructions to enable the kit to be used in the methods described herein or details regarding which subjects the method may be used for.

As explained above, the compounds of the invention are useful in treating or preventing bacterial infection. In particular, they are useful as inhibitors of LasB, in particular LasB of *Pseudomonas aeruginosa* (PA). The compounds may be used alone or they may be used in combination therapies with antibiotic agents, to enhance the action of the antibiotic agent. The present invention therefore also provides a combination comprising (i) a compound of the invention as described herein and (ii) an antibiotic agent. The combination may further comprise one or more additional active agents. The compound of the invention and the antibiotic agent may be provided in a single formulation, or they may be separately formulated. Where separately formulated, the two agents may be administered simultaneously or separately. They may be provided in the form of a kit, optionally together with instructions for their administration.

Where formulated together, the two active agents may be provided as a pharmaceutical composition comprising (i) a compound of the invention as described herein and (ii) a further antibacterial compound; and (iii) a pharmaceutically acceptable carrier or diluent.

Preferably, the antibiotic agent is efficacious against *Pseudomonas* infection. Most preferably, the antibiotic is tobramycin, neomycin, streptomycin, gentamycin, ceftazidime, ticarcillin, piperacillin, tazobactam, imipenem, meropenem, rifampicin, ciprofloxacin, amikacin, colistin, aztreonam, azithromycin or levofloxacin. More preferably, the antibiotic is tobramycin, neomycin, streptomycin, gentamycin, ceftazidime, ticarcillin, piperacillin, tazobactam, imipenem, meropenem, rifampicin, ciprofloxacin, amikacin, colistin, aztreonam or levofloxacin.

The compound or combination of the invention may be administered in a variety of dosage forms. Thus, they can be administered orally, for example as tablets, troches, lozenges, aqueous or oily suspensions, dispersible powders or granules. They may also be administered parenterally, whether subcutaneously, intravenously, intramuscularly, intrasternally, transdermally or by infusion techniques. The compound or combination may also be administered as a suppository. Preferably, the compound or combination may be administered via inhaled (aerosolised) or intravenous administration, most preferably by inhaled (aerosolised) administration.

The compound or combination of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

The compound or combination of the invention may be formulated for inhaled (aerosolised) administration as a solution or suspension. The compound or combination of the invention may be administered by a metered dose inhaler (MDI) or a nebulizer such as an electronic or jet nebulizer. Alternatively, the compound or combination of the invention may be formulated for inhaled administration as a powdered drug, such formulations may be administered from a dry powder inhaler (DPI). When formulated for inhaled administration, the compound or combination of the invention may be delivered in the form of particles which have a mass median aerodynamic diameter (MMAD) of from 1 to 100 µm, preferably from 1 to 50 µm, more preferably from 1 to 20 µm such as from 3 to 10 µm, e.g. from 4 to 6 µm. When the compound or combination of the invention is delivered as a nebulized aerosol, the reference to particle diameters defines the MMAD of the droplets of the aerosol. The MMAD can be measured by any suitable technique such as laser diffraction.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections or inhalation may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for inhalation, injection or infusion may contain as carrier, for example, sterile water or preferably they may be in the form of sterile, aqueous, isotonic saline solutions. Pharmaceutical compositions suitable for delivery by needleless injection, for example, transdermally, may also be used.

Therapeutic Efficacy

The compounds, compositions and combinations of the present invention are therapeutically useful. The present invention therefore provides compounds, compositions and combinations as described herein, for use in medicine. The present invention provides compounds as described herein, for use in treating the human or animal body. For the avoidance of doubt, the agent may comprise a compound of the invention in the form of a solvate.

The compounds, compositions and combinations of the invention are useful in treating or preventing bacterial infection. The present invention therefore provides a compound, combination or composition as described herein for use in a method of treating or preventing bacterial infection in a subject in need thereof. Also provided is a method for treating or preventing bacterial infection in a subject in need thereof, which method comprises administering to said subject an effective amount of a compound, combination or composition as described herein. Further provided is the use of a compound, combination or composition as described herein in the manufacture of a medicament for use in treating or preventing bacterial infection in a subject.

The compounds described herein are useful as inhibitors of LasB, in particular LasB of *Pseudomonas aeruginosa* (PA). The inhibition of LasB in the bacteria prevents LasB secreted by bacteria from hydrolysing host tissue and host immune-response proteins, thereby supporting the subject in its natural response to bacterial infection and inflammation. The compounds described herein are therefore useful as standalone adjuncts in antibacterial therapy, for example in chemotherapy regimes. Further, the compounds are useful in inhibiting biofilm formation, and/or in disrupting a biofilm. This activity in preventing biofilm formation or disrupting established biofilms facilitates antibiotic agents in eradication of bacterial infection. It also facilitates the host's own immune system in attacking the bacterial infection. The compounds may therefore be used as stand alone antibacterial agents.

Alternatively, the compounds described herein may be used in combination with antibiotic agents to enhance the action of the antibiotic agent. Therefore, further provided is a compound of the invention as described herein for use in a method of treating or preventing bacterial infection by co-administration with an antibiotic agent. Also provided is a method for treating or preventing bacterial infection in a subject in need thereof, which method comprises co-administering to said subject an effective amount of a compound as described herein and an antibiotic agent. Also provided is the use of a compound as described herein in the the manufacture of a medicament for use in treating or preventing bacterial infection by co-administration with an antibiotic agent.

In one aspect, the subject is a mammal, in particular a human. However, it may be non-human. Preferred non-human animals include, but are not limited to, primates, such as marmosets or monkeys, commercially farmed animals, such as horses, cows, sheep or pigs, and pets, such as dogs, cats, mice, rats, guinea pigs, ferrets, gerbils or hamsters. The subject can be any animal that is capable of being infected by a bacterium.

The compounds, compositions and combinations described herein are useful in the treatment of bacterial infection which occurs after a relapse following an antibiotic treatment. The compounds and combinations can therefore be used in the treatment of a patient who has previously received antibiotic treatment for the (same episode of) bacterial infection.

The bacterium causing the infection may be any bacterium expressing LasB or an analogue thereof. Typically the bacterium causing the infection expresses LasB. The bacterium may, for instance, be any bacterium that can form a biofilm. The bacterium may be Gram-positive or Gram-negative. In a preferred instance the bacterium is Gram-negative. The bacterium may in particular be a pathogenic bacterium.

The bacterial infection may be caused by *Bacillus, Pseudomonas, Staphylococcus, Streptococcus, Listeria, Escherichia* or *Burkholderia*. For example, the bacterium may be one selected from *Staphylococcus aureus, Haemophilus influenza, Pseudomonas aeruginosa* and *Burkholderia cepacia*.

In one preferred instance, the bacterium may be one selected from a bacterium of the family Pseudomonadaceae. For example, the bacterium may be selected from one of the following genera: *Pseudomonas, Azomonas, Azomonotrichon, Azorhizophilus, Azotobacter, Cellvibrio, Mesophilobacter, Rhizobacter, Rugamonas* and *Serpens*. Preferably the bacterium is a *Pseudomonas*, particularly where the condition to be treated is pneumonia. The bacterium may be an opportunistic pathogen. The bacterium may be selected from *Pseudomonas aeruginosa, Pseudomonas oryzihabitans*, and *Pseudomonas plecoglossicida*, and most preferably, the bacterium is *Pseudomonas aeruginosa* (PA).

The compound, composition or combination of the invention may be used to treat or prevent infections and conditions caused by any one or a combination of the above-mentioned bacteria. In particular, the compound or combination of the invention may be used in the treatment or prevention of pneumonia. The compound or combination may also be used in the treatment of septic shock, urinary tract infection, and infections of the gastrointestinal tract, skin or soft tissue.

The compounds, compositions and combinations described herein may also be used to treat or prevent inflammation in a subject. Without being bound by theory, such utility is believed to arise from the activity of the compounds to inhibit the activation of the pro-inflammatory cytokine interleukin-1-$\beta$ (IL-1$\beta$), e.g. by inhibiting activity of LasB enzymes (such as PA LasB) to activate IL-1$\beta$ by hydrolysis of pro-IL-1$\beta$ at a distinct site from caspase-1. Accordingly, the compounds, compositions and combinations described herein are particularly suitable for treating inflammation caused by or associated with IL-1$\beta$ activation in a subject. The compounds, compositions and combinations described herein are especially suitable in treating or preventing bacterial inflammation caused by or associated with IL-1$\beta$ activation in a subject, particularly when the bacteria causing the infection express one or more LasB enzymes or analogs thereof.

Typically, the compounds, compositions and combinations described herein are especially suitable in treating or preventing respiratory tract inflammation in a subject. The respiratory tract inflammation may be inflammation of any part of the respiratory tract, in particular the lower respiratory tract (e.g. inflammation of the trachea, bronchi or lungs). The compounds described herein are particularly suited to treating or preventing pulmonary inflammation in a subject. The respiratory tract inflammation (e.g. pulmonary inflammation) is typically caused by a bacterial infection, especially by an infection caused by bacteria which express one or more LasB enzymes or analogs thereof, as described above. In some aspects the respiratory tract inflammation (e.g. pulmonary inflammation) is caused by an infection caused by a bacterium of the family Pseudomonadaceae, such as a *Pseudomonas aeruginosa* (PA) infection.

The compounds, compositions and combinations described herein are useful for treating or preventing inflammation in a subject in need thereof. As described in more detail below, the compounds, compositions and combinations described herein are useful in the treatment of patients suffering from cystic fibrosis. The compounds, compositions and combinations described herein are also useful in the treatment of patients suffering from other conditions associated with bacterial inflammation, such as chronic obstructive pulmonary disease (COPD), bronchiectasis, and/or ventilator-associated pneumonia (VAP).

The compounds and combinations are particularly useful in the treatment of patients suffering from cystic fibrosis. Preferably, the compound or combination of the invention may be used in the treatment or prevention of pneumonia in a subject suffering from cystic fibrosis. For example, the subject may have any of the six CFTR mutation classes, and/or may be infected by or chronically colonised by PA. The compounds and combinations of the invention may also be used in the treatment of neutropenic patients.

A compound or combination of the invention can be administered to the subject in order to prevent the onset or reoccurrence of one or more symptoms of the bacterial infection. This is prophylaxis. In this embodiment, the subject can be asymptomatic. The subject is typically one that has been exposed to the bacterium. A prophylactically effective amount of the agent or formulation is administered to such a subject. A prophylactically effective amount is an amount which prevents the onset of one or more symptoms of the bacterial infection.

A compound or combination of the invention can be administered to the subject in order to treat one or more symptoms of the bacterial infection. In this embodiment, the subject is typically symptomatic. A therapeutically effective amount of the agent or formulation is administered to such a subject. A therapeutically effective amount is an amount effective to ameliorate one or more symptoms of the disorder.

A therapeutically or prophylactically effective amount of the compound of the invention is administered to a subject. The dose may be determined according to various parameters, especially according to the compound used; the age, weight and condition of the subject to be treated; the route of administration; and the required regimen. Again, a physician will be able to determine the required route of administration and dosage for any particular subject. A typical daily dose is from about 0.01 to 100 mg per kg, preferably from about 0.1 mg/kg to 50 mg/kg, e.g. from about 1 to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

Other Uses

The antibacterial properties of the compounds described herein mean that they are also useful in the treatment of bacterial infection in vitro, i.e. other than by the treatment of human or animal subjects. Thus, also described herein is a cleaning composition comprising a indane derivative of Formula (I) or a salt thereof. The cleaning composition may further comprise, for example, a detergent, a surfactant (including ionic and non-ionic surfactants), a diluent, a bleach (including a hypochlorite such as sodium hypochlorite or calcium hypochlorite, chlorine, chlorine dioxide, hydrogen peroxide or an adduct thereof, sodium perborate, and sodium percarbonate), an alcohol (such as ethanol or isopropanol), or a disinfectant. Typically, the disinfectant may be selected from benzyl-4-chlorophenol, amylphenol, phenylphenol, glutaraldehyde, alkyl dimethyl benzyl ammonium chloride, alkyl dimethyl ethylbenzyl ammonium chloride, iodine, peracetic acid and chlorine dioxide. Typically, the detergent may be an alkaline detergent such as sodium hydroxide, sodium metasilicate, or sodium carbonate, or an acid detergent such as hydrochloric acid, nitric acid, sulfuric acid, phosphoric acid, citric acid, or tartaric acid.

Also described herein is the use of the indane derivative of Formula (I) as described herein for the prevention or treatment of bacterial contamination in vitro. Such use may be an in vitro method for the prevention or treatment of bacterial infection which comprises a step of treatment of an object with a compound or combination of the invention. Such use is a non-therapeutic use and may involve, for example, prevention or treatment of bacterial contamination on a surface, such as a surface of an indwelling medical device, or an object used in a clinical setting. The surface may be the surface of a catheter, a nebulizer, a ventilator, or a face mask. Typically, the bacterial contamination is caused by any bacteria described herein. Preferably, the bacteria is *Pseudomonas aeruginosa*.

The following Examples illustrate the invention. They do not however, limit the invention in any way. In this regard, it is important to understand that the particular assay used in the Examples section is designed only to provide an indication of biological activity. There are many assays available to determine biological activity, and a negative result in any one particular assay is therefore not determinative.

EXPERIMENTAL DETAILS

General Synthetic Methodology

As described below, there are two synthetic methodologies to synthesize the compounds of the invention.

Method A. Regiospecific Synthesis of Key Intermediate (3)

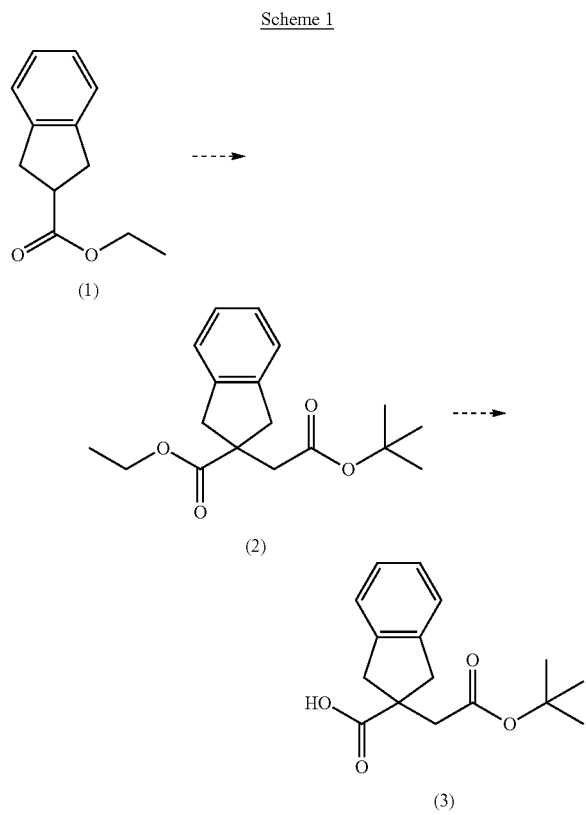

Deprotonation of commercially available ethyl ester (1) with strong base (such as sodium hexamethyldisilazide) then alkylation of the anion with tert-butyl bromoacetate gives known diester (2) (Bell, I. M. and Stump, C. A., WO2006/29153; Robinson, R. P. et al, Bioorganic and Medicinal Chemistry Letters, 1996, 1719). Basic hydrolysis of the ethyl ester in the presence of the tert-butyl ester gives (3). Amide formation with a suitable 2-aminomethyl benzothiazole followed by treatment with TFA to remove the tert-butyl ester then affords the desired acids. The acids can be converted to esters ($R^1=R^{1a}$) or other prodrug forms ($R^1=CH_2OC(O)R^{1a}$) by techniques known to the skilled person.

This methodology can be adapted to substituents on the indane ring.

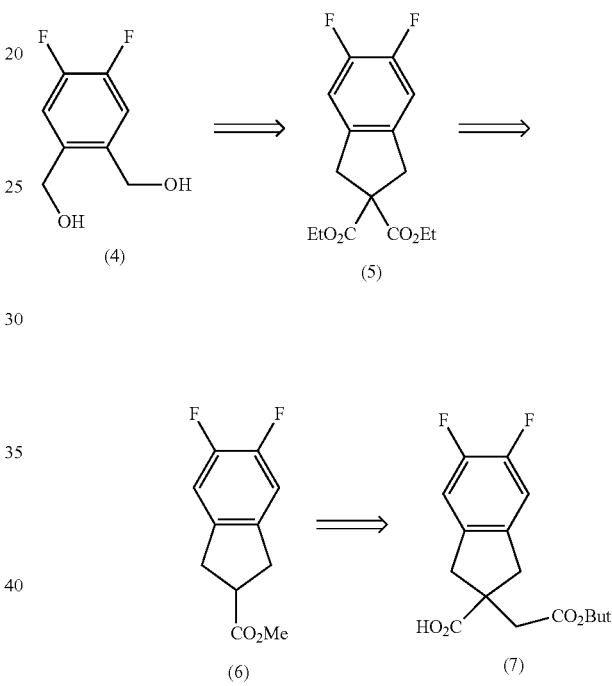

For example commercially available diol [4,5-difluoro-2-(hydroxymethyl)phenyl]methanol (4) can be converted into the bis bromomethyl analogue with either HBr (WO2008/151211) or phosphorus tribromide (US2006/223830) which can further be reacted with diethyl malonate to give indane (5), (Scheme 2). Standard hydrolysis of both esters followed by mono decarboxylation affords the mono acid (WO2006/125511) which can be esterified to give (6), the difluoro analogue of (1). Using the same methodology as applied to (1) then affords key acid (7), the difluoro analogue of intermediate (3). Similar chemistry can be applied to the corresponding analogues having different substituents on the indane ring.

There are numerous ways of accessing hydroxamic acids (for a review see Ganeshpurkar, A., et al, Current Organic Syntheses, 2018, 15, 154-165) but a very reliable procedure is to couple acids (64) with O-(oxan-2-yl)hydroxylamine using peptide coupling conditions to give protected hydroxamates (65) then deprotect with TFA to generate the hydroxamic acids (66), (see for example Ding, C., et al, Bioorg. Med. Chem. Lett, 2017, 25, 27-37).

Method B. Synthesis of Protected 2-Aminomethyl Benzothiazoles

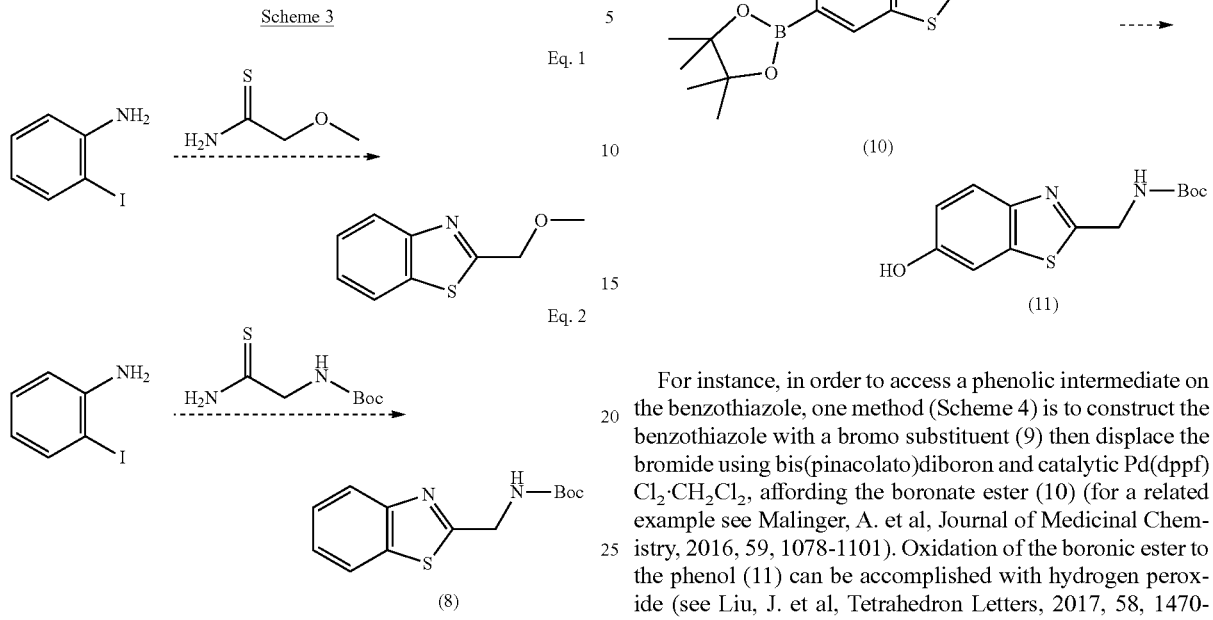

There are many ways of constructing benzothiazoles (for a review, see Seth, S; "A Comprehensive Review on Recent advances in Synthesis & Pharmacotherapeutic potential of Benzothiazoles", Anti-Inflammatory & Anti-Allergy Agents in Medicinal Chemistry, 2015, 14, 98-112). However, most methods afford alkyl substitution at the C2-position necessitating further functional group manipulation to access the desired aminomethyl substituent required in this invention. In the 1980's the pioneering work of Takagi and colleagues led to a palladium-catalysed method of directly producing functionalised methyl groups (see Eq. 1, Scheme 3; Takagi, K. et al, Chemistry Letters, 1987, 16, 839-840). This chemistry was recently rediscovered by *mutabilis* scientists who adapted the methodology to introduce a protected aminomethyl group into the benzothiazole core (8), (see Eq. 2, Scheme 3; Desroy, N., et al, Journal of Medicinal Chemistry, 2013, 56, 1418-1430). Application of this methodology accesses the protected 2-aminomethyl benzothiazoles of this invention.

Method C. Functional Group Manipulation on Protected Aminomethylbenzothiazole

In many cases the desired substituent pattern on the phenyl ring can be established prior to benzothiazole formation using standard functional group transformations. In certain cases it is preferred to perform functional group transformations after benzothiazole formation.

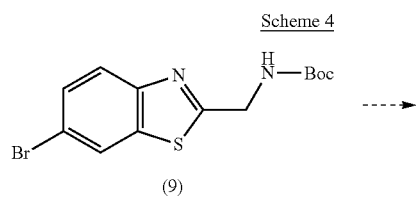

For instance, in order to access a phenolic intermediate on the benzothiazole, one method (Scheme 4) is to construct the benzothiazole with a bromo substituent (9) then displace the bromide using bis(pinacolato)diboron and catalytic Pd(dppf)Cl$_2$·CH$_2$Cl$_2$, affording the boronate ester (10) (for a related example see Malinger, A. et al, Journal of Medicinal Chemistry, 2016, 59, 1078-1101). Oxidation of the boronic ester to the phenol (11) can be accomplished with hydrogen peroxide (see Liu, J. et al, Tetrahedron Letters, 2017, 58, 1470-1473.) Further derivatisation of the phenol group can be achieved by standard alkylation reactions familiar to those skilled in the art.

Method D. Final Stages to Synthesise the Examples

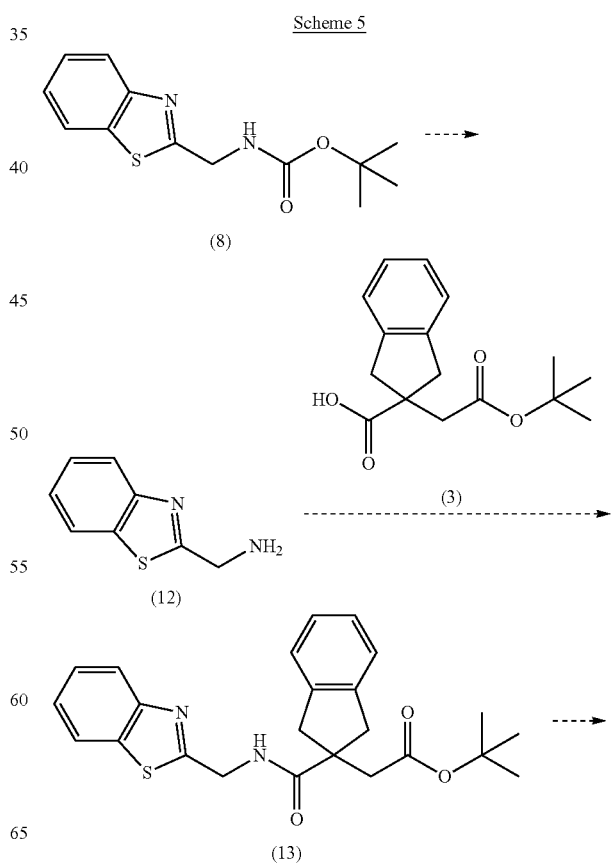

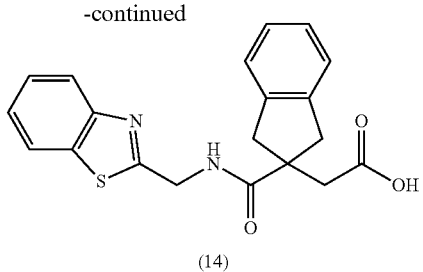

(14)

The final stages of the syntheses generally involve acid-catalysed removal of the BOC group from (8) to reveal the free amines (12) followed by coupling with acids of type (3), usually with the standard peptide coupling reagent HATU (for a comprehensive review of the myriad available peptide coupling reagents, see Valeur, E. and Bradley, M, Chem. Soc. Rev., 2008, 28, 606-631). Finally further acid treatment with TFA removes the t-butyl ester to afford the Examples of the invention.

Method E. Functional Group Manipulation after Amide Coupling of Aminomethylbenzothiazole and Indanyl Moieties Scheme 6

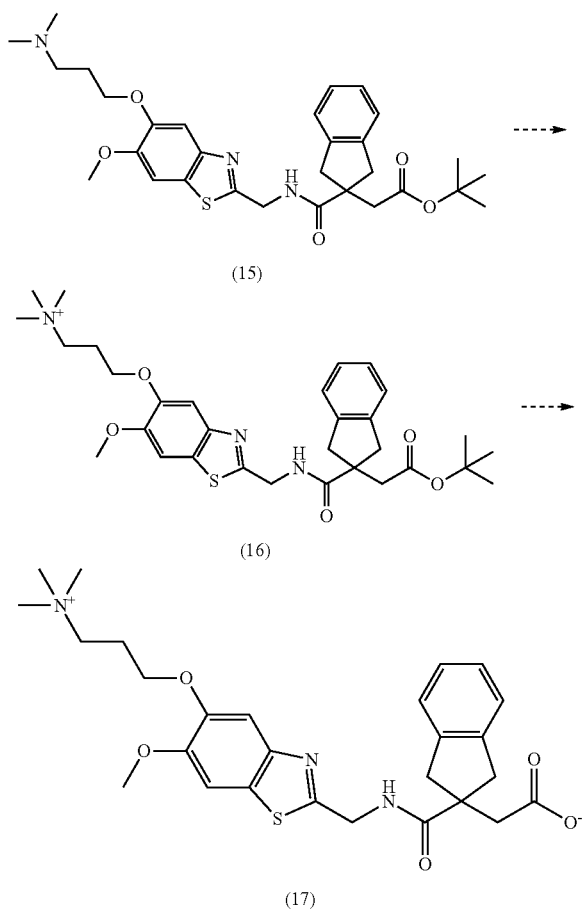

As an example of this approach, alkylation of tert-butyl N-[(5-hydroxy-6-methoxy-1,3-benzothiazol-2-yl)methyl] carbamate with 3-chloro-N,N-dimethylpropan-1-amine, removal of the tert-butoxycarbonyl protecting group and coupling with acid (3) can generate the N,N-dimethylaminopropyloxy intermediate (15). Reaction with an alkylating agent such as iodomethane then generates the corresponding quaternary ammonium salt (16) and finally removal of the tert-butyl ester reveals the carboxylate acid, generating zwitterionic (17) containing both a positive and a negative charge.

It is understood that these synthetic routes are not exclusive and functional group interconversion is possible at the phenyl precursor stage, the protected aminomethyl benzothiazole stage and the post-coupling amide stage.

EXAMPLES

1H NMR spectra are reported at 300, 400 or 500 MHz in DMSO-d6 solutions ($\delta$ in ppm), using DMSO-$d_5$ as reference standard (2.50 ppm), or CDCl$_3$ solutions using chloroform as the reference standard (7.26 ppm). When peak multiplicities are reported, the following abbreviations are used: s (singlet), d (doublet), t (triplet), m (multiplet), bs (broadened singlet), bd (broadened doublet), dd (doublet of doublets), dt (doublet of triplets), q (quartet). Coupling constants, when given, are reported in hertz (Hz).

The term "purified by prep hplc (MDAP)" refers compound purification using a mass-directed auto purification system on an Agilent 1260 infinity machine with an XSelect CHS Prep C18 column, eluting with 0.1% FA in water/ACN and detection with a Quadrupole LC/MS.

ABBREVIATIONS

ACN Acetonitrile
AcOH Acetic acid
aq. Aqueous
Bpin Bis(pinacolato)diboron
CaCl$_2$ Calcium chloride
Cs$_2$CO$_3$ Cesium carbonate
cfu Colony forming unit
Conc Concentrated
Cu(OAc)$_2$ Copper(II) acetate
CuO Copper oxide
DCM Dichloromethane
DEA Diethylamine
DIPEA N,N-Diisopropylethylamine
DMAP 4-Dimethylaminopyridine
DMF N,N-Dimethylformamide
DMSO Dimethyl sulfoxide
dppf 1,1'-Bis(diphenylphosphino)ferrocene
EDC·HCl N-(3-Dimethylaminopropyl)-N'-ethylcarbodiimide hydrochloride
Et$_2$O Diethyl ether
EtOAc Ethyl acetate
EtOH Ethanol
Et$_3$N Triethylamine
Ex Excitation
FA Formic acid
FCC Flash column chromatography purification on silica
h Hour(s)
HATU 1-[Bis(dimethylamino)methylene]-1H-1,2,3-triazolo[4,5-b]pyridinium 3-oxid hexafluorophosphate
HCl Hydrochloric acid/hydrochloride salt
HOBt Hydroxybenzotriazole
H$_2$SO$_4$ Sulfuric Acid
Km Michaelis constant
KOAc Potassium acetate
KOH Potassium hydroxide
MeCN Acetonitrile MeI Methyl iodide
MeOH Methanol
min Minute(s)
MgSO₄ Magnesium sulfate
N₂ Nitrogen
NBS N-bromo succinimide
Na₂CO₃ Sodium carbonate
NaHCO₃ Sodium bicarbonate
NaHMDS Sodium bis(trimethylsilyl)amide
Na₂SO₄ Sodium sulfate
Pd₂(dba)₃ Tris(dibenzylideneacetone)dipalladium(0)
PdCl₂(dppf) [1,1'-Bis(diphenylphosphino)ferrocene]dichloropalladium(II)
RT Room temperature
SCX-2 Strong cation exchange resin (silica-propyl sulfonic acid)
T % B Time, % solvent B
TES Triethylsilane
TFA Trifluoroacetic acid
THF Tetrahydrofuran
T3P Propylphosphinic anhydride Example 1 2-[2-[[6-(3-hydroxypropoxy)-1,3-benzothiazol-2-yl]methylcarbamoyl]indan-2-yl]acetic acid

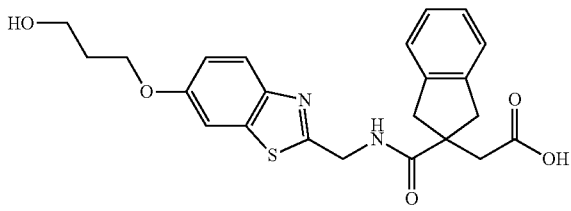 [SMILES: O=C(O)CC1(C(=O)NCc2nc3ccc(OCCCO)cc3s2)Cc2ccccc2C1]

a. Tert-butyl N-[(6-bromo-1,3-benzothiazol-2-yl)methyl]carbamate

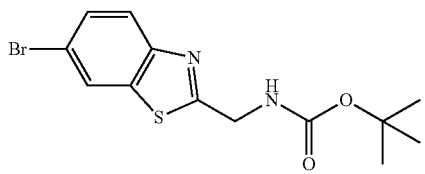 [SMILES: CC(C)(C)OC(=O)NCc1nc2ccc(Br)cc2s1]

To a stirred solution of 4-bromo-2-iodo-aniline (3 g, 10.13 mmol) and tert-butyl (2-amino-2-thioxoethyl) carbamate (1.92 g, 10.13 mmol) in DMF (30 mL) was added CuO (0.8 g, 10.13 mmol) at room temperature and the reaction mixture was degassed with argon for 15 minutes. Then Dppf (280 mg, 0.50 mmol) and Pd₂(dba)₃ (185.4 mg, 0.20) were added and the resulting reaction mixture was degassed with argon for further 5 minutes. The reaction mixture was stirred in sealed tube at 60° C. for 3h, and then filtered through celite pad and washed the pad with EtOAc (50 mL). The filtrate was washed with water (2×30 mL) and concentrated under reduced pressure. The crude compound was purified by silica gel chromatography eluting with 22% EtOAc in petroleum ether affording as a yellow solid (5 g, 72%). M/z 343 (M+H)⁺.

b. Tert-butyl N-[[6-(4,4,5,5-tetramethyl-1,3,2-dioxaborolan-2-yl)-1,3-benzothiazol-2-yl]methyl]carbamate

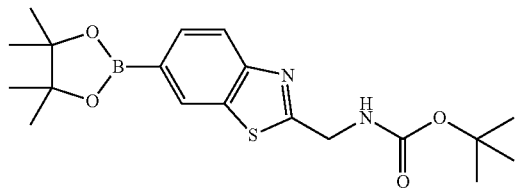 [SMILES: CC(C)(C)OC(=O)NCc1nc2ccc(B3OC(C)(C)C(C)(C)O3)cc2s1]

To a stirred solution of tert-butyl N-[(6-bromo-1,3-benzothiazol-2-yl)methyl]carbamate (1.3 g, 3.80 mmol), and bis(pinacolato)diboron (1.44 g, 5.70 mmol) in 1,4-dioxane (15 mL) was added KOAc (745 mg, 7.60 mmol) at room temperature and the reaction mixture was purged with argon for 15 minutes. Then PdCl₂(dppf)·DCM (155 mg, 0.190 mmol) was added and the reaction mixture purged with argon for further 5 minutes. The reaction mixture was stirred to reflux in sealed tube for 12 h, and then filtered through celite pad and washed with EtOAc (50 mL). The filtrate was washed with water (2×30 mL), the organic layer was dried with sodium sulphate, filtered and concentrated under reduced pressure to get a brown solid (1.5 g, crude). M/z 391.2 (M+H)⁺.

c. Tert-butyl N-[(6-hydroxy-1,3-benzothiazol-2-yl)methyl]carbamate

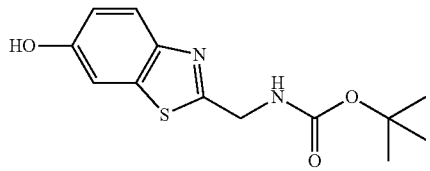 [SMILES: CC(C)(C)OC(=O)NCc1nc2ccc(O)cc2s1]

To a stirred solution of tert-butyl N-[[6-(4,4,5,5-tetramethyl-1,3,2-dioxaborolan-2-yl)-1,3-benzothiazol-2-yl]methyl]carbamate (1.5 g, 3.84 mmol) in THF (15 mL) was added 1N NaOH (3.84 mL g, 3.84 mmol) at 0° C. and stirred for 10 minutes. Then H₂O₂ (30% in H₂O, 0.21 mL, 8.84 mmol) was added at 0° C. and the reaction mixture stirred to room temperature for 1 h. The reaction mixture was partitioned between ethyl acetate (100 mL) and water (70 mL). The aqueous phase was extracted with ethyl acetate (2×100 mL) and the combined organic extracts were washed with brine, dried with Na₂SO₄, filtered and evaporated. The crude product was purified by silica gel chromatography eluting with 40% EtOAc in petroleum ether affording a white solid (1.0 g, 93.4%). M/z 281.1 (M+H)⁺.

d. Tert-butyl N-[[6-(3-hydroxypropoxy)-1,3-benzo-thiazol-2-yl]methyl]carbamate

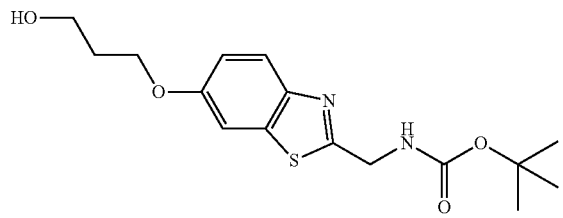 [SMILES: CC(C)(C)OC(=O)NCc1nc2ccc(OCCCO)cc2s1]

To a solution of tert-butyl N-[(6-hydroxy-1,3-benzothiazol-2-yl)methyl]carbamate (300 mg, 1.07 mmol) in DMF (5 mL) was added K$_2$CO$_3$ (222 mg, 1.60 mmol), 3-bromopropan-1-ol (224 mg, 1.60 mmol) at room temperature and heated at 80° C. for 2 h. The reaction mixture was diluted with water (20 mL) and extracted with EtOAc (2×30 mL). The combined organic extract was dried, filtered and evaporated. The crude was purified by silica gel chromatography eluting with 45-60% EtOAc in petroleum ether affording a yellow solid (210 m, 58%). M/z=338.9 (M+H)$^+$.

e. 3-[[2-(aminomethyl)-1,3-benzothiazol-6-yl]oxy]propan-1-ol hydrochloride

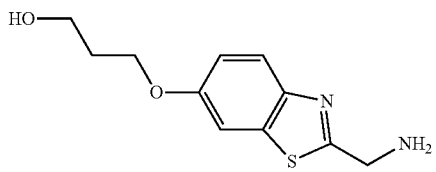 [SMILES: NCc1nc2ccc(OCCCO)cc2s1]

To a solution of tert-butyl N-[[6-(3-hydroxypropoxy)-1,3-benzothiazol-2-yl]methyl]carbamate (210 mg, 0.62 mmol) in dioxane (5 mL) was added 4M HCl in dioxane (2 mL) at room temperature and stirred for 3 h. The reaction mixture was evaporated and the resulting residue was triturated with diethyl ether (20 mL) affording an off white solid (165 mg, crude). M/z=238.9 (M+H)$^+$.

f. Methyl Indane-2-carboxylate

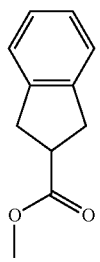

To a stirred solution of 2,3-dihydro-1H-indene-2-carboxylic acid (20 g, 123 mmol) in methanol (200 mL) was added conc. H$_2$SO$_4$ (10 mL, 185 mmol) drop wise at room temperature and stirred at 80° C. for 16 h. The reaction mixture was evaporated to get residue. The residue was dissolved in water (100 mL) and extracted with EtOAc (2×100 mL). The organic layer was washed with sat. sodium bicarbonate, brine and evaporated affording a light brown liquid (20 g, 92%). M/z 177.1 (M+H)$^+$.

g. Methyl 2-(2-tert-butoxy-2-oxo-ethyl)indane-2-carboxylate

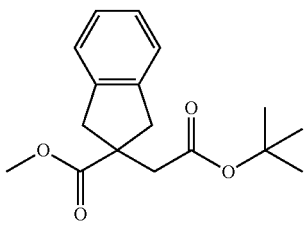 [SMILES: COC(=O)C1(CC(=O)OC(C)(C)C)Cc2ccccc2C1]

To a solution of methyl 2,3-dihydro-1H-indene-2-carboxylate (5 g, 28.3 mmol) in THF (100 mL) was added NaHMDS (21 mL, 42.5 mmol, 2M in THF) at −78° C. under argon and stirred at −78° C. for 1 h. Then tert-butyl 2-bromoacetate solution (6.4 mL, 42.5 mmol) in THF (30 mL) was added drop wise for 15 minutes at −78° C. and stirred at same temperature for 2 h. The reaction mixture was quenched with sat. ammonium chloride solution (50 mL) at −78° C. and allowed to stir at room temperature for 30 minutes. The organic layer was separated, aqueous layer was extracted with EtOAc (2×100 mL), and the combined organic layer was evaporated to get crude compound. The crude compound was triturated with n-pentane (50 mL) at −78° C. and stirred at same temperature for 15 minutes. The resulting solid was filtered and dried under vacuum affording an off white solid (3.7 g, 45%). M/z=313.0 (M+Na)$^+$.

h. 2-(2-tert-butoxy-2-oxo-ethyl)indane-2-carboxylic acid

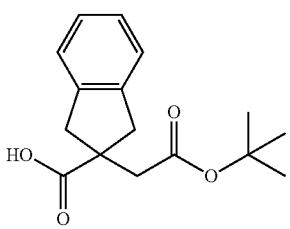 [SMILES: CC(C)(C)OC(=O)CC1(C(=O)O)Cc2ccccc2C1]

To a stirred solution of methyl 2-(2-(tert-butoxy)-2-oxo-ethyl)-2,3-dihydro-1H-indene-2-carboxylate (430 g, 1.48 mol) in THF (2.15 L) and ethanol (2.15 L) was added 0.5 M LiOH·H$_2$O (6.8 L, 2.96 mol) drop wise at room temperature and stirred at same temperature for 2 h. The reaction mixture was evaporated to get the residue and the residue was diluted with H$_2$O (1 L) and extracted with diethyl ether. The aqueous layer was acidified with 1N HCl to pH 3-4. The resulting precipitate was filtered, washed with water, n-pentane and dried under vacuum affording a white solid (254.5 g, 62%). M/z 275.2 (M−H)$^−$. $^1$H NMR (300 MHz, DMSO-d$_6$): δ 12.4 (1H, bs), 7.18-7.10 (4H, m), 3.39 (2H, d, J=16.2 Hz), 2.92 (2H, d, J=16.2 Hz), 2.64 (2H, s), 1.37 (9H, s).

i. Tert-butyl 2-[2-[[6-(3-hydroxypropoxy)-1,3-benzothiazol-2-yl]methylcarbamoyl]indan-2-yl]acetate

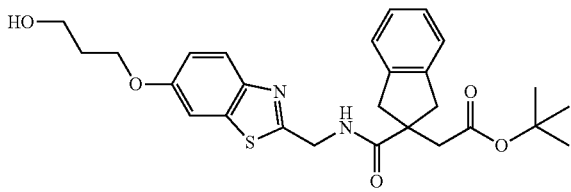 [SMILES: CC(C)(C)OC(=O)CC1(C(=O)NCc2nc3ccc(OCCCO)cc3s2)Cc2ccccc2C1]

To a solution of 2-(2-(tert-butoxy)-2-oxoethyl)-2,3-dihydro-1H-indene-2-carboxylic acid (150 mg, 0.54 mmol) in DMF (6 mL) was added Et$_3$N (0.2 mL, 1.62 mmol), EDC.HCl (125 mg, 0.65 mmol), HOBt (74 mg, 0.54 mmol) and 3-[[2-(aminomethyl)-1,3-benzothiazol-6-yl]oxy]propan-1-ol hydrochloride (164 mg, 0.59 mmol) at room temperature and stirred for 12 h. The reaction mixture was diluted with cold water (20 mL) and extracted with EtOAc (2×30 mL) and evaporated. The crude was purified by silica gel chromatography with 3-5% MeOH in DCM affording a yellow solid (125 mg, 46%). M/z=497.2 (M+H)$^+$.

j. 2-[2-[[6-(3-hydroxypropoxy)-1,3-benzothiazol-2-yl]methylcarbamoyl]indan-2-yl]acetic acid To a solution of tert-butyl 2-[2-[[6-(3-hydroxypropoxy)-1,3-benzothiazol-2-yl]methylcarbamoyl]indan-2-yl]acetate (110 mg, 0.22 mmol) in DCM (5 mL) was added TFA (2 mL) at 0° C. and stirred at room temperature for 2 h. The mixture was evaporated and the residue was triturated with diethyl ether (15 mL). The crude compound was purified by preparative HPLC [HPLC [SYMMETRY-C8 (300*19 mm), 7 u, Mobile phase: A: 0.1% Formic Acid in H$_2$O, B: MeCN] affording the title compound as an off white solid (20 mg, 20%). M/z 441.1 (M+H)$^+$. $^1$H NMR (500 MHz, DMSO-d$_6$): δ 12.12 (1H, bs), 8.69 (1H, t, J=6 Hz), 7.79 (1H, d, J=9 Hz), 7.57 (1H, d, J=2.5 Hz), 7.22-7.19 (2H, m), 7.15-7.13 (2H, m), 7.06 (1H, dd, J=9 Hz, J=2.5 Hz), 4.60 (2H, d, J=6 Hz), 4.55 (1H, t, J=5 Hz), 4.08 (2H, t, J=6.5 Hz), 3.57 (2H, td, J=6 Hz, J=5 Hz), 3.44 (2H, d, J=16 Hz), 3.00 (2H, d, J=16 Hz), 2.73 (2H, s), 1.89-1.86 (2H, m).

Example 2 2-[2-[(6-propoxy-1,3-benzothiazol-2-yl)methylcarbamoyl]indan-2-yl]acetic acid

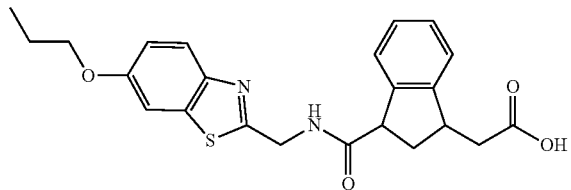 [SMILES: CCCOc1ccc2nc(CNC(=O)C3CC(CC(=O)O)c4ccccc43)sc2c1]

This was prepared in an analogous manner to Example 1 using 1-bromopropane in step-d. The title compound was isolated as white solid (37 mg, 38%). M/z 425.1 (M+H)$^+$. $^1$H NMR (500 MHz, DMSO-d$_6$): δ 12.14 (1H, bs), 8.97 (1H, bs), 7.78 (1H, d, J=9 Hz), 7.56 (1H, d, J=2.5 Hz), 7.21-7.20 (2H, m), 7.14-7.12 (2H, m), 7.06 (1H, dd, J=9.0 Hz, J=2.5 Hz), 4.60 (2H, d, J=5.5 Hz), 3.98 (2H, t, J=6.5 Hz), 3.47 (2H, d, J=16.5 Hz), 3.00 (2H, d, J=16 Hz), 2.70 (2H, s), 1.77-1.72 (2H, m), 1.00 (3H, t, J=7.5 Hz).

Example 3 2-[2-[[5-[3-(dimethylamino)propoxy]-6-methoxy-1,3-benzothiazol-2-yl]methylcarbamoyl] indan-2-yl]acetic acid

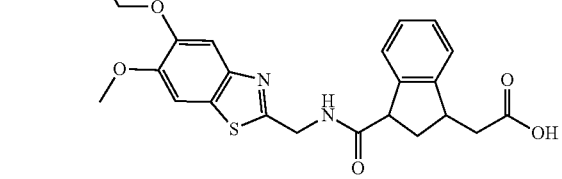

a. 4-bromo-5-methoxy-2-nitroaniline

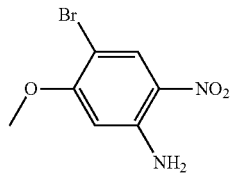

To a stirred solution of 5-methoxy-2-nitroaniline (100 g, 595 mmol) in acetonitrile (2.5 L) was added NBS (106 g, 595 mmol) portion wise at room temperature. The mixture was cooled to 0° C. and added TFA (46 mL, 595 mmol) drop wise for 30 minutes and allowed to stir at room temperature for 16 h. The reaction mixture was diluted with water (1 L) and adjusted the pH to ~8 with 1N NaOH. The resulting precipitate was filtered, washed with water (500 mL) and dried under vacuum affording a yellow solid. (105 g, 72%). M/z 247 (M+H)$^+$.

b. 1-Bromo-4-iodo-2-methoxy-5-nitrobenzene

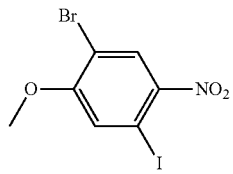

To a stirred solution of 4-bromo-5-methoxy-2-nitroaniline (50 g, 203 mmol) in acetonitrile (750 mL) was added concentrated H$_2$SO$_4$ (24 mL, 457 mmol) drop wise at −10° C. Then NaNO$_2$ (28 g, 406 mmol) in water (175 mL) was added drop wise at −10° C. for 15 minutes and stirred at same temperature for 30 min. After that KI solution (135 g, 813 mmol) in water (175 mL) was added drop wise at −10° C. for 20 minutes and stirred at same temperature for 30 min. The reaction mixture was quenched with sodium metabisulphite solution (309 g, 1.62 mmol) in water (1.6 L) at −10° c. 5-Bromo-2-iodo-4-methoxyaniline

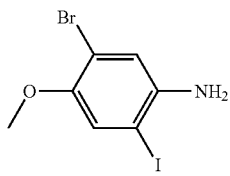

To a stirred solution of 1-bromo-4-iodo-2-methoxy-5-nitrobenzene (106 g, 296 mmol) in EtOH: $H_2O$ (800 mL: 200 mL) was added Fe (49.7 g, 890 mmol), $NH_4Cl$ (80 g, 1.48 mmol) at room temperature and stirred at 90° C. for 2 h. Then the reaction mixture was cooled to 60° C., added additional amount of Fe (33 g, 593 mmol), $NH_4Cl$ (80 g 1.48 mmol) and stirred at 90° C. for 30 minutes. The reaction mixture was filtered through ciliate pad, washed the pad with methanol (1 L) and filtrate was concentrated to give residue. The residue was diluted with cold water (1 L) and adjusted the pH to 8 with 1N NaOH. The resulting precipitate was filtered and dried under vacuum affording a light brown solid (90 g, 92%). M/z 327.8 $(M+H)^+$.

d. Tert-butyl N-[(5-bromo-6-methoxy-1,3-benzothiazol-2-yl)methyl]carbamate

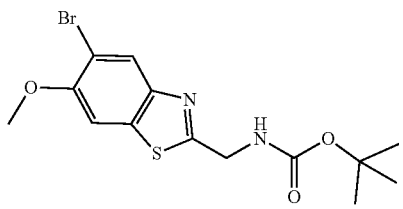 [SMILES: COc1cc2sc(CNC(=O)OC(C)(C)C)nc2cc1Br]

To a stirred solution of 5-bromo-2-iodo-4-methoxyaniline (50 g, 152 mmol) in acetonitrile (560 mL) was added tert-butyl(2-amino-2-thioxoethyl)carbamate (35 g, 183 mmol), CaO (17 g, 305 mmol) and degassed with argon for 20 minutes. Then $Pd_2(dba)3$ (14 g, 15.2 mmol), dppf (25.4 g, 15.8 mmol) was added and purged with argon for further 5 minutes and the reaction mixture was stirred at 80° C. for 4 hour. The reaction mixture was filtered through celite pad and washed the pad with EtOAc (300 mL). The filtrate was washed with water and evaporated to get crude compound. The crude compound was dissolved in acetonitrile (200 mL), on standing for 1 hour solid was precipitated out. The resulting solid was filtered, washed with acetonitrile (50 mL) and dried under vacuum affording an off white solid (34 g, 60%). M/z 372.9 $(M+H)^+$.

e. Tert-butyl N-[[6-methoxy-5-(4,4,5,5-tetramethyl-1,3,2-dioxaborolan-2-yl)-1,3-benzothiazol-2-yl]methyl]carbamate

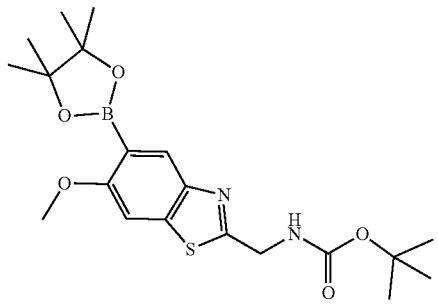 [SMILES: COc1cc2sc(CNC(=O)OC(C)(C)C)nc2cc1B1OC(C)(C)C(C)(C)O1]

To a stirred solution of tert-butyl ((5-bromo-6-methoxy-benzo[d]thiazol-2-yl)methyl)carbamate (5 g, 13.44 mmol) in dioxane (100 mL) was added BPin (6.8 g, 26.8 mmol), KOAc (4.6 g, 47.0 mmol) and purged with argon for 15 minutes. Then $Pd_2Cl_2(dppf)$. DCM (1.1 g, 1.34 mmol) was added and purged with argon for further 5 minutes. The reaction mixture was heated at 100° C. for 16 h. The reaction mixture was filtered through celite pad and washed the pad with EtOAc (50 mL). The filtrate was washed with water, brine and evaporated affording a white solid (12 g, crude). M/z 339 $(M+H)^+$.

f. Tert-butyl N-[(5-hydroxy-6-methoxy-1,3-benzothiazol-2-yl)methyl]carbamate

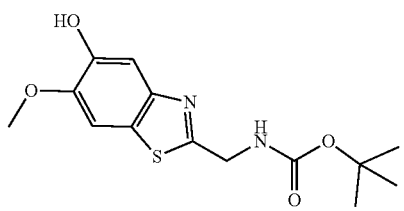 [SMILES: COc1cc2sc(CNC(=O)OC(C)(C)C)nc2cc1O]

To a stirred solution of tert-butyl N-[[6-methoxy-5-(4,4,5,5-tetramethyl-1,3,2-dioxaborolan-2-yl)-1,3-benzothiazol-2-yl]methyl]carbamate (12 g, 35.5 mmol) in THF (180 mL) was added 1N NaOH (35 mL, 35.5 mmol), 30% $H_2O_2$ (6.2 mL 81.6 mmol) at 0° C. and stirred at same temperature for 30 minutes. The reaction mixture was partitioned between water and EtOAc. The organic layer was separated washed with water, brine and evaporated to get crude compound. The crude compound was chromatographed on silica eluting with 30% EtOAc in pet ether affording an off white solid. (2.5 g 54%). M/z 311.0 $(M+H)^+$. $^1H$ NMR (500 MHz, $CDCl_3$): δ 7.50 (1H, s), 7.25 (1H, s), 5.76 (1H, s), 5.30 (1H, s), 4.68 (2H, d, J=5.5 Hz), 3.97 (3H, s), 1.54 (9H, s). M/z 311.0 $(M+H)^+$.

g. Tert-butyl N-[[5-[3-(dimethylamino)propoxy]-6-methoxy-1,3-benzothiazol-2-yl]methyl]carbamate

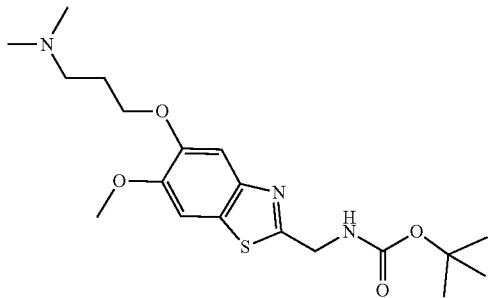 [SMILES: COc1cc2sc(CNC(=O)OC(C)(C)C)nc2cc1OCCCN(C)C]

To a solution of tert-butyl N-[(5-hydroxy-6-methoxy-1,3-benzothiazol-2-yl)methyl]carbamate (750 mg, 2.41 mmol) in DMF (5 mL) was added $K_2CO_3$ (1 g, 7.25 mmol), 3-chloro-N,N-dimethylpropan-1-amine (355 mg, 2.90 mmol) at room temperature and heated at 80° C. for 4 h. The reaction mixture was diluted with water (25 mL) and extracted with EtOAc (2×30 mL). The combined organic layer was dried, filtered and evaporated affording a pale brown liquid (1 g, crude). M/z 395.8 (M+H)$^+$.

h. 3-[[2-(aminomethyl)-6-methoxy-1,3-benzothiazol-5-yl]oxy]-N,N-dimethyl-propan-1-amine hydrochloride

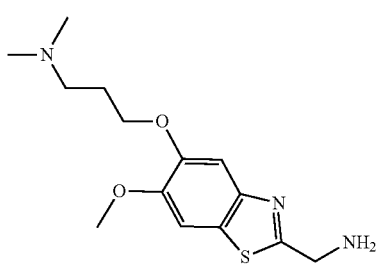 [SMILES: COc1cc2sc(CN)nc2cc1OCCCN(C)C]

To a solution of tert-butyl N-[[5-[3-(dimethylamino)propoxy]-6-methoxy-1,3-benzothiazol-2-yl]methyl]carbamate (1 g, 2.53 mmol) in dioxane (5 mL) was added 4M HCl in dioxane (6 mL) at room temperature and stirred for 6 h. The reaction mixture was evaporated and the resulting residue was triturated with diethyl ether (25 mL) affording a pale yellow solid (0.92 g, crude). M/z 296.2 (M+H)$^+$.

i. Tert-butyl 2-[2-[[5-[3-(dimethylamino)propoxy]-6-methoxy-1,3-benzothiazol-2-yl]methylcarbamoyl]indan-2-yl]acetate

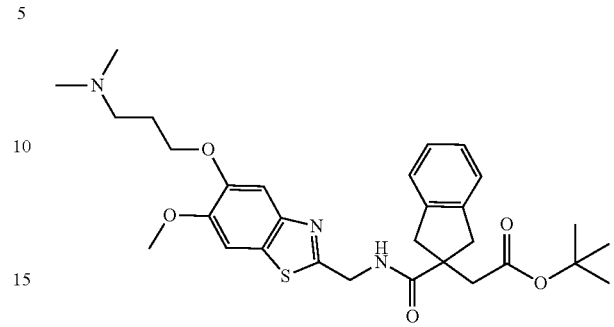

To a solution of 3-[[2-(aminomethyl)-6-methoxy-1,3-benzothiazol-5-yl]oxy]-N,N-dimethyl-propan-1-amine hydrochloride (450 mg, 1.52 mmol) in DMF (6 mL) was added $Et_3N$ (1.1 mL, 7.62 mmol) and stirred for 10 minutes. Then 2-(2-(tert-butoxy)-2-oxoethyl)-2,3-dihydro-1H-indene-2-carboxylic acid (463 mg, 1.67 mmol), EDC. HCl (440 mg, 2.28 mmol) and HOBt (210 mg, 1.52 mmol) was added at room temperature and stirred for 16 h. The reaction mixture was diluted with cold water (30 mL) and extracted with EtOAc (2×40 mL) and evaporated to get crude compound. The crude was chromatographed on silica eluting with 10-12% MeOH in DCM affording a yellow solid (310 mg, 56%). M/z 554.2 (M+H)$^+$.

j. 2-[2-[[5-[3-(dimethylamino)propoxy]-6-methoxy-1,3-benzothiazol-2-yl]methylcarbamoyl]indan-2-yl]acetic acid To a solution of tert-butyl 2-[2-[[5-[3-(dimethylamino)propoxy]-6-methoxy-1,3-benzothiazol-2-yl]methylcarbamoyl]indan-2-yl]acetate (120 mg, 0.21 mmol) in DCM (5 mL) was added TFA (2 mL) at 0° C. and stirred at room temperature for 2 h. The mixture was evaporated and the residue was triturated with diethyl ether (15 mL). The crude compound was purified by preparative HPLC [YMC-TRIART (150×25 mm), 10 u, Mobile phase: A: 0.1% Formic Acid in $H_2O$, B: MeCN] affording the title compound as an off white solid (32 mg, 30%). M/z 498.1 (M+H)$^+$. $^1$H NMR (500 MHz, DMSO-$d_6$): δ 9.00 (1H, bs), 7.55 (1H, s), 7.43 (1H, s), 7.21-7.20 (2H, m), 7.14-7.12 (2H, m), 4.60 (2H, d, J=6 Hz), 4.04 (2H, t, J=6.5 Hz), 3.81 (3H, s), 3.45 (2H, d, J=16 Hz), 2.98 (2H, d, J=16 Hz), 2.69 (2H, s), 2.40 (2H, t, J=7 Hz), 2.17 (6H, s), 1.91-1.85 (2H, m).

Example 4 2-[2-[[6-methoxy-5-[3-(trimethylammonio)propoxy]-1,3-benzothiazol-2-yl]methylcarbamoyl]indan-2-yl]acetate

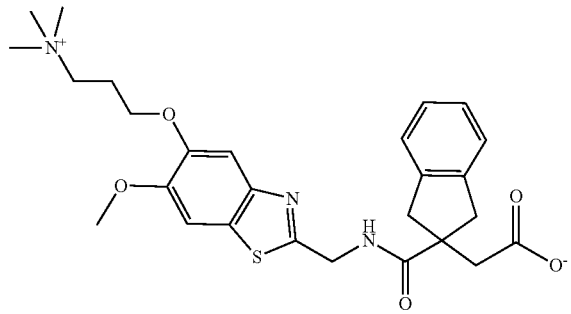 [SMILES: COc1cc2sc(CNC(=O)C3(CC(=O)[O-])Cc4ccccc4C3)nc2cc1OCCC[N+](C)(C)C]

a. 3-[[2-[[[2-(2-tert-butoxy-2-oxo-ethyl)indane-2-carbonyl]amino]methyl]-6-methoxy-1,3-benzothiazol-5-yl]oxy]propyl-trimethyl-ammonium iodide

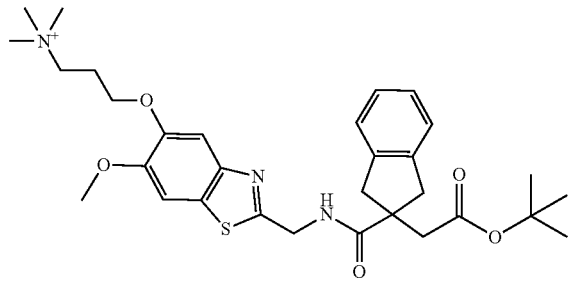 [SMILES: COc1cc2sc(CNC(=O)C3(CC(=O)OC(C)(C)C)Cc4ccccc4C3)nc2cc1OCCC[N+](C)(C)C]

To a solution of tert-butyl 2-[2-[[5-[3-(dimethylamino)propoxy]-6-methoxy-1,3-benzothiazol-2-yl]methylcarbamoyl]indan-2-yl]acetate (200 mg, 0.36 mmol) in acetonitrile (5 mL) was added MeI (1 mL) at 0° C. and stirred at room temperature for 16 h. The mixture was evaporated and resulting residue was purified by silica gel chromatography eluting with 15-20% 7M NH$_3$/MeOH in DCM affording a pale yellow solid (100 mg, 49%). M/z 568.3 (M)$^+$.

b. 2-[2-[[6-methoxy-5-[3-(trimethylammonio)propoxy]-1,3-benzothiazol-2-yl]methylcarbamoyl]indan-2-yl]acetate To a solution of 3-[[2-[[[2-(2-tert-butoxy-2-oxo-ethyl)indane-2-carbonyl]amino]methyl]-6-methoxy-1,3-benzothiazol-5-yl]oxy]propyl-trimethyl-ammonium iodide (90 mg, 0.15 mmol) in DCM (5 mL) was treated with TFA (1.5 mL) at 0° C. and stirred at room temperature for 4 h. The mixture was evaporated and the residue was triturated with diethyl ether (10 mL). The crude compound was purified by preparative HPLC [X-BRIDGE-C18 (150*30), 5 u, Mobile phase: A: 0.1% Formic Acid in H$_2$O, B: MeCN] affording the title compound as an off white solid (8.2 mg, 10%). M/z 512.3 (M+H)$^+$. $^1$H NMR (500 MHz, DMSO-d$_6$): 12.27 (1H, bs), 7.64 (1H, s), 7.53 (1H, s), 7.17-7.15 (2H, m), 7.11-7.09 (2H, m), 4.61 (2H, d, J=5.5 Hz), 4.12 (2H, t, J=6 Hz), 3.82 (3H, s), 3.51-3.49 (2H, m), 3.40 (2H, d, J=16 Hz), 3.10 (9H, s), 2.90 (2H, d, J=16 Hz), 2.40 (2H, s), 2.24-2.21 (2H, m).

Example 5 2-[2-[[6-methoxy-5-[2-[2-(trimethylammonio)ethoxy]ethoxy]-1,3-benzothiazol-2-yl]methylcarbamoyl]indan-2-yl]acetate

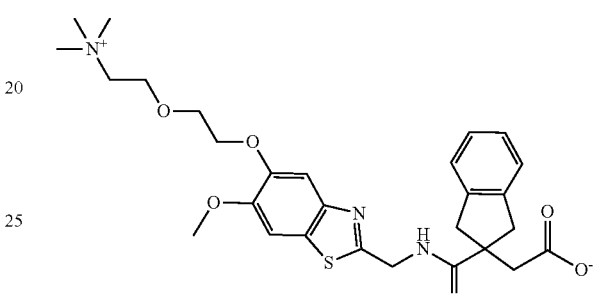

c. Tert-butyl N-[[5-[2-(2-chloroethoxy)ethoxy]-6-methoxy-1,3-benzothiazol-2-yl]methyl]carbamate

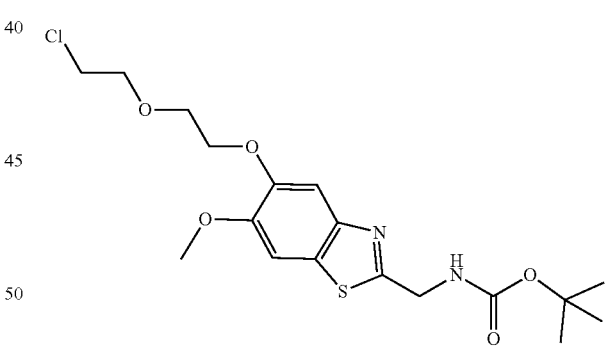

A solution of tert-butyl N-[(5-hydroxy-6-methoxy-1,3-benzothiazol-2-yl)methyl]carbamate (600 mg, 1.93 mmol) in acetonitrile (10 mL) was added Cs$_2$CO$_3$ (692 mg, 2.12 mmol) and 1-chloro-2-(2-chloroethoxy)ethane (304 mg, 2.12 mmol) at room temperature. The mixture was heated at 70° C. for 16 h, then filtered through celite pad and washed the pad with EtOAc (15 mL). The filtrate was concentrated and the residue was chromatographed on silica eluting with 25% EtOAc in petroleum ether affording an off white solid (250 mg, 32%). M/z 417.1 (M+H)$^+$ d. Tert-butyl N-[[5-[2-[2-(dimethylamino)ethoxy]ethoxy]-6-methoxy-1,3-benzothiazol-2-yl]methyl]carbamate

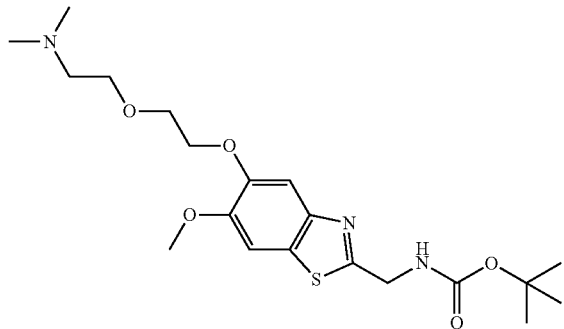 [SMILES: COc1cc2sc(CNC(=O)OC(C)(C)C)nc2cc1OCCOCCN(C)C]

A solution of tert-butyl ((5-(2-(2-chloroethoxy)ethoxy)-6-methoxybenzo[d]thiazol-2-yl)methyl)carbamate (250 mg, 0.60 mmol) in acetone (5 mL) was added Cs$_2$CO$_3$ (293 mg, 0.90 mmol) and dimethylamine (2 mL, 2M in THF) at 0° C. The mixture was heated at 90° C. in a sealed tube for 20 h. The reaction mixture was filtered through celite pad and washed the pad with EtOAc (15 mL). The filtrate was concentrated and the residue was chromatographed on silica eluting with 10-20% MeOH in DCM affording a pale yellow solid (210 mg, 84%). M/z 426.2 (M+H)$^+$ e. 2-(2-((2-(aminomethyl)-6-methoxybenzo[d]thiazol-5-yl)oxy)ethoxy)-N,N-dimethylethan-1-amine hydrochloride

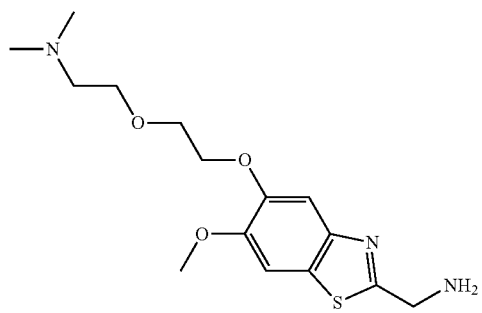 [SMILES: COc1cc2sc(CN)nc2cc1OCCOCCN(C)C]

A solution of tert-butyl ((5-(2-(2-(dimethylamino)ethoxy)ethoxy)-6-methoxybenzo[d]thiazol-2-yl)methyl)carbamate (200 mg, 0.47 mmol) in dioxane (4 mL) was added 4M HCl in dioxane (5 mL) at room temperature. The mixture was stirred at room temperature for 4 h and concentrated under reduced pressure. The residue was triturated with diethyl ether (10 mL) affording an off white solid (180 mg, crude). M/z 326.1 (M+H)$^+$.

f. Tert-butyl 2-[2-[[5-[2-[2-(dimethylamino)ethoxy]ethoxy]-6-methoxy-1,3-benzothiazol-2-yl]methylcarbamoyl]indan-2-yl]acetate

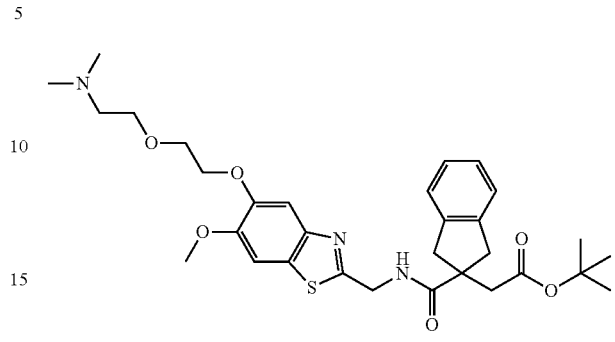

A solution of 2-(2-((2-(aminomethyl)-6-methoxybenzo[d]thiazol-5-yl)oxy)ethoxy)-N,N-dimethylethan-1-amine hydrochloride (300 mg, 0.92 mmol) in DMF (8 mL) was added Et$_3$N (0.4 mL, 2.76 mmol) and stirred for 10 minutes. Then 2-(2-(tert-butoxy)-2-oxoethyl)-2,3-dihydro-1H-indene-2-carboxylic acid (280 mg, 1.01 mmol) and T3P (0.9 mL, 1.38 mmol) was added at room temperature and stirred for 16 h. The reaction mixture was partitioned between water (15 mL) and EtOAc (30 mL). The organic layer was evaporated and resulting crude compound was chromatographed on silica eluting with 10%-20% MeOH in DCM affording an off white solid (200 mg, 38%). M/z 584.2 (M+H)$^+$.

g. 2-[2-[[2-[[[2-(2-tert-butoxy-2-oxo-ethyl)indane-2-carbonyl]amino]methyl]-6-methoxy-1,3-benzothiazol-5-yl]oxy]ethoxy]ethyl-trimethyl-ammonium

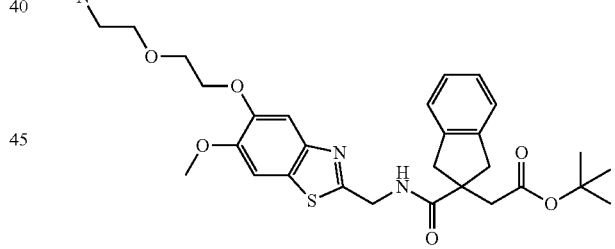

A solution of tert-butyl 2-(2-(((5-(2-(2-(dimethylamino)ethoxy)ethoxy)-6-methoxybenzo[d]thiazol-2-yl)methyl)carbamoyl)-2,3-dihydro-1H-inden-2-yl)acetate (200 mg, 0.34 mmol) in acetonitrile (5 mL) was added MeI (1 mL) at 0° C. and stirred at room temperature for 8 h. The mixture was evaporated and the residue was purified by preparative TLC eluting with 10% MeOH in DCM affording an off white solid (60 mg, 30%). M/z 598.1 (M)$^+$.

h. 2-[2-[[6-methoxy-5-[2-[2-(trimethylammonio)ethoxy]ethoxy]-1,3-benzothiazol-2-yl]methylcarbamoyl]indan-2-yl]acetate A solution of 2-(2-((2-(2-(tert-butoxy)-2-oxoethyl)-2,3-dihydro-1H-indene-2-carboxamido)methyl)-6-methoxybenzo[d]thiazol-5-yl)oxy)ethoxy)-N,N,N-trimethylethan-1-aminium (120 mg, 0.20 mmol) in DCM (5 mL) was treated with TFA (1 mL) at 0° C. and stirred at room temperature for 4 h. The mixture was evaporated and the residue was triturated with diethyl ether (10 mL). The crude compound was purified by preparative HPLC [X-BRIDGE-C18 (150*30), 5 u, Mobile phase: A: 0.1% Formic Acid in $H_2O$, B: MeCN] and freeze dried affording the title product as an off white solid (46 mg, 43%). M/z 542.2 $(M+H)^+$. $^1$H NMR (500 MHz, DMSO-$d_6$): δ 9.85 (1H, bs), 7.58 (1H, s), 7.49 (1H, s), 7.20-7.18 (2H, m), 7.13-7.11 (2H, m), 4.60 (2H, d, J=5.0 Hz), 4.20 (2H, t, J=4 Hz), 3.94 (2H, bs), 3.85 (2H, t, J=4 Hz), 3.82 (3H, s), 3.53 (2H, t, J=4.5 Hz), 3.43 (2H, d, J=16 Hz), 3.10 (9H, s), 2.96 (2H, d, J=16 Hz), 2.62 (2H, s).

Example 6 2-[5,6-difluoro-2-[[6-methoxy-5-[2-[2-(trimethylammonio)ethoxy]ethoxy]-1,3-benzothiazol-2-yl]methylcarbamoyl]indan-2-yl]acetate

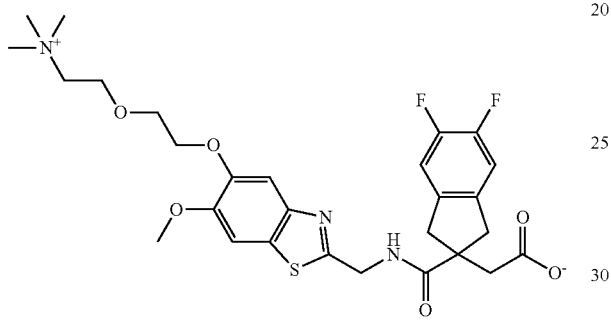

a. Dimethyl 4,5-difluorophthalate

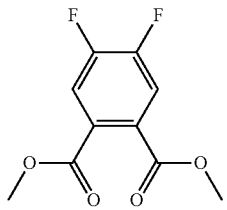

To an ice-cooled solution of 4,5-difluorophthalic acid (11.9 g, 58.9 mmol) in MeOH (250 mL) was added concentrated $H_2SO_4$ (40 mL, 0.75 mol) keeping the temperature <20° C. The mixture was stirred at 65° C. for 4 h. The cooled reaction mixture was concentrated in vacuo, then the residue was cautiously added to EtOAc and aq. $NaHCO_3$. The aq. phase was extracted with EtOAc and the combined organic extracts were washed with aq. $NaHCO_3$, then brine, dried ($Na_2SO_4$), filtered and concentrated in vacuo to yield the title compound as a colourless oil (12.98 g, 96%). $^1$H NMR ($CDCl_3$) δ 7.56 (2H, t, J=8.7 Hz), 3.91 (6H, s).

b. (4,5-Difluoro-1,2-phenylene)dimethanol

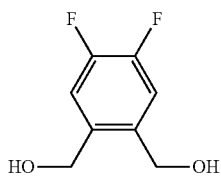 [SMILES: OCc1cc(F)c(F)cc1CO]

To an ice-cooled solution of lithium aluminium hydride (1M in THF, 226 mL, 0.226 mol) was added a solution of dimethyl 4,5-difluorophthalate (12.98 g, 56.4 mmol) in THF (100 mL) over 30 min keeping the temperature below 12° C. The mixture was stirred in the ice bath for 30 min, then at RT for 1 h. The reaction mixture was cooled to 0° C. then, cautiously, water (8.5 mL), 15% aq. NaOH (8.5 mL) and water (26 mL) were added successively, keeping the temperature below 15° C. Celite was added and the mixture stirred at RT for 1 h, then filtered through a celite pad, washing through with more THF. The filtrate was concentrated in vacuo to yield the title compound as a white solid (9.52 g, 97%). $^1$H NMR (d6-DMSO) δ 7.36 (2H, t, J=10.1 Hz), 5.29 (2H, t, J=5.5 Hz), 4.47 (4H, d, J=5.4 Hz).

c. 1,2-Bis(bromomethyl)-4,5-difluorobenzene

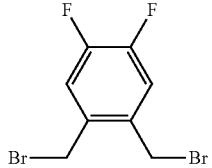

A mixture of (4,5-difluoro-1,2-phenylene)dimethanol (9.52 g, 54.7 mmol) and 48% hydrobromic acid (68.5 mL) was stirred at 110° C. for 1 h. The cooled reaction mixture was diluted with water and then extracted with $Et_2O$. The aq. phase was extracted with $Et_2O$ and the combined organic extracts were washed with water, then brine, dried ($Na_2SO_4$), filtered and concentrated in vacuo to leave a residue. FCC (1-10% EtOAc in hexane) to yield the title compound as a colourless oil (15.2 g, 93%). $^1$H NMR ($CDCl_3$) δ 7.20 (2H, t, J=9.1 Hz), 4.55 (4H, s).

d. Diethyl 5,6-difluoro-1,3-dihydro-2H-indene-2,2-dicarboxylate

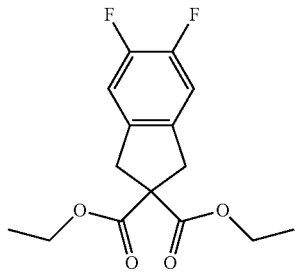 [SMILES: CCOC(=O)C1(C(=O)OCC)Cc2cc(F)c(F)cc2C1]

Sodium hydride (60% in oil, 4.46 g, 112 mmol) was added over 15 min to a mixture of 1,2-bis(bromomethyl)-4,5-difluorobenzene (15.2 g, 50.7 mmol) and diethyl malonate (9.74 g, 60.8 mmol) in THF (200 mL) keeping the temperature below 20° C. The mixture was stirred at RT for 4 h, then saturated ammonium chloride was added. The mixture was concentrated in vacuo and then extracted twice with EtOAc. The combined organic extracts were washed with brine, dried ($Na_2SO_4$), filtered and concentrated in vacuo to leave a residue. FCC (5-25% EtOAc in hexane) yielded the title compound as a colourless oil (9.95 g, 66%). $^1$H NMR ($CDCl_3$) δ 6.97 (2H, t, J=8.7 Hz), 4.21 (4H, q, J=7.1 Hz), 3.52 (4H, s), 1.26 (6H, t, J=7.1 Hz).

e. 5,6-Difluoro-2,3-dihydro-1H-indene-2-carboxylic acid

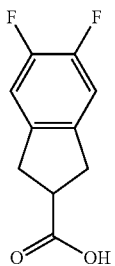

To a solution of diethyl 5,6-difluoro-1,3-dihydro-2H-indene-2,2-dicarboxylate (9.94 g, 33.3 mmol) in dioxane (130 mL) was added water (130 mL) and concentrated HCl (140 mL). The mixture was refluxed for 23 h. The cooled reaction mixture was diluted with water and extracted with $Et_2O$ (×3). The combined organic extracts were washed with water, then brine, dried ($Na_2SO_4$) and concentrated in vacuo to yield the title compound as a colourless solid (6.6 g, quant.). M/z 197 (M−H)$^-$.

f. Methyl 5,6-difluoro-2,3-dihydro-1H-indene-2-carboxylate

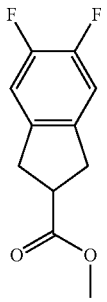

To an ice-cooled solution of 5,6-difluoro-2,3-dihydro-1H-indene-2-carboxylic acid (6.6 g, 33.3 mmol) in MeOH (200 mL) was added concentrated $H_2SO_4$ (40 mL, 0.75 mol) keeping the temperature <20° C. The mixture was stirred at 65° C. for 1 h. The cooled reaction mixture was concentrated in vacuo, then the residue was cautiously added to EtOAc and aq. $NaHCO_3$. The aq. phase was extracted with more EtOAc and the combined organic extracts were washed with brine, dried ($Na_2SO_4$), filtered and concentrated in vacuo to leave a residue. FCC (5-25% EtOAc in hexane) yielded the title compound as a pale yellow solid (5.97 g, 84%). $^1$H NMR ($CDCl_3$) δ 6.98 (2H, t, J=8.8 Hz), 3.73 (3H, s), 3.39 (1H, m), 3.24-3.12 (4H, m).

g. Methyl 2-(2-(tert-butoxy)-2-oxoethyl)-5,6-difluoro-2,3-dihydro-1H-indene-2-carboxylate

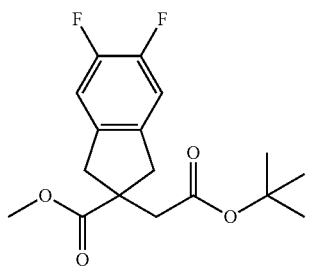 [SMILES: COC(=O)C1(CC(=O)OC(C)(C)C)Cc2cc(F)c(F)cc2C1]

To a solution of methyl 5,6-difluoro-2,3-dihydro-1H-indene-2-carboxylate (5.97 g, 28.2 mmol) in THF (120 mL), cooled to −78° C., was added sodium bis(trimethylsilyl)amide (1M in THF, 42.2 mL, 42.2 mol) over 15 min. The mixture was stirred at −78° C. for 45 min then a solution of tert-butyl bromoacetate (8.24 g, 42.2 mmol) in THF (15 mL) was added over 10 min. The reaction mixture was allowed to warm to −10° C. over 1 h. Saturated ammonium chloride was added and the mixture was concentrated under reduced pressure. The residue was extracted twice with EtOAc and the combined organic extracts were washed with brine, dried ($Na_2SO_4$), filtered and concentrated in vacuo to leave a residue. FCC (5-20% EtOAc in hexane) yielded the title compound as a yellow gum (8.78 g, 96%). $^1$H NMR ($CDCl_3$) δ 6.96 (2H, t, J=8.9 Hz), 3.72 (3H, s), 3.47 (2H, d, J=16.2 Hz), 2.90 (2H, d, J=16.2 Hz), 2.71 (2H, s), 1.42 (9H, s).

h. 2-[(tert-butoxy)carbonyl]-5,6-difluoro-2,3-dihydro-1H-indene-2-carboxylic acid

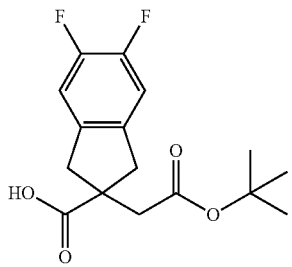 [SMILES: CC(C)(C)OC(=O)CC1(C(=O)O)Cc2cc(F)c(F)cc2C1]

To a solution of methyl 2-(2-(tert-butoxy)-2-oxoethyl)-5,6-difluoro-2,3-dihydro-1H-indene-2-carboxylate (0.834 g, 2.56 mmol) in THF (25 mL) and MeOH (10 mL) was added lithium hydroxide (0.5M in water, 10.2 mL, 5.1 mmol). The mixture was stirred at RT for 2.5 h, then concentrated in vacuo. The residual solution was layered with EtOAc and acidified by addition of 6M HCl. The aq. phase was extracted with more EtOAc and the combined organic extracts were washed with brine, dried ($Na_2SO_4$), filtered and concentrated in vacuo to leave a residue. FCC (2-6% MeOH in DCM) yielded the title compound as a cream solid (0.59 g, 74%). $^1$H NMR (d6-DMSO) δ 12.47 (1H, bs), 7.26 (2H, t, J=9.2 Hz), 3.33 (2H, d, J=16.4 Hz), 2.91 (2H, d, J=16.4 Hz), 2.67 (2H, s), 1.37 (9H, s). M/z 311 (M−H)$^−$.

i. 2-[5,6-difluoro-2-[[6-methoxy-5-[2-[2-(trimethylammonio)ethoxy]ethoxy]-1,3-benzothiazol-2-yl]methylcarbamoyl]indan-2-yl]acetate This was prepared in an analogous manner to Example 5 using 2-[(tert-butoxy)carbonyl]-5,6-difluoro-2,3-dihydro-1H-indene-2-carboxylic acid in step-d. The title compound was isolated as an orange solid (58.5 mg). M/z 578.5 (M+H)$^+$. $^1$H NMR (500 MHz, DMSO-d$_6$): δ 13.05 (1H, bs), 7.60 (1H, s), 7.61 (1H, s), 7.22-7.21 (1H, m), 7.17-7.14 (1H, m), 4.62 (2H, d, J=6 Hz), 4.21 (2H, m), 3.93 (2H, m), 3.87 (2H, s), 3.82 (3H, s), 3.58 (2H, m), 3.36 (2H, m), 3.10 (9H, s), 2.89-2.81 (2H, m), 2.32 (2H, m).

Example 7 2-[5,6-difluoro-2-[[6-methoxy-5-[2-(trimethylammonio)ethoxy]-1,3-benzothiazol-2-yl]methylcarbamoyl]indan-2-yl]acetate

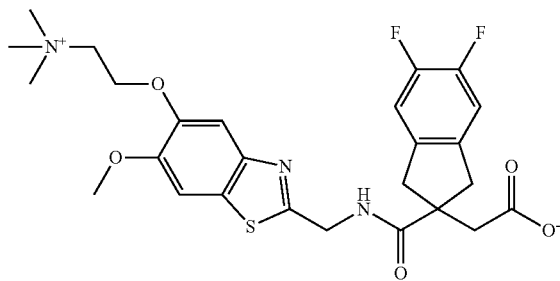 [SMILES: COc1cc2sc(CNC(=O)C3(CC(=O)[O-])Cc4cc(F)c(F)cc4C3)nc2cc1OCC[N+](C)(C)C]

This was prepared in an analogous manner to Example 5 using in 2-Chloro-N,N-dimethylethylamine hydrochloride in step-a and 2-[(tert-butoxy)carbonyl]-5,6-difluoro-2,3-dihydro-1H-indene-2-carboxylic acid in step-d. The title compound was isolated as a white solid (13 mg, 12%). M/z 534.3 (M+H)$^+$. $^1$H NMR (500 MHz, DMSO-d$_6$): δ 13.16 (1H, bs), 7.69 (1H, s), 7.63 (1H, s), 7.22-7.21 (1H, m), 7.17-7.14 (1H, m), 4.61 (2H, m), 4.53 (2H, m), 3.82 (5H, m), 3.32 (2H, m), 3.21 (9H, s), 2.89-2.81 (2H, m), 2.32 (2H, m).

Example 8: LasB Inhibitory Activity Measurements

The relevance of LasB to PA infection has been shown in experiments measuring lung burden in a rat model of chronic lung infection following infection with WT PA (which expresses LasB) and a mutant form of PA (ΔlasB PA) in which LasB is not expressed. It could be clearly seen in that following infection, whereas a wild type strain is able to persist at least for 14 days, a LasB deficient strain was not able to persist beyond day 5. The relevance of LasB to PA biofilm development was also shown. Biofilms formed after 3 days by both PA26 wt and PA26 lasB deletion strains were investigated by confocal imaging and subsequent analysis (with Comstat software). This study demonstrated that biofilms formed by the PA26 lasB deletion strain were highly reduced in thickness and biomass compared to the wt strain, demonstrating the essential role of LasB in PA biofilm development.

The relevance of LasB to *Pseudomonas aeruginosa* (PA) infection is illustrated in FIG. 1, which shows incidence of mortality versus survival, and chronic colonisation versus bacterial clearance, in a mouse model of lung infection. Chronicity of the infection is defined by PA lung burden higher than 10^3 CFU seven days after infection. In this infection model, both wild type strain (expressing LasB; "wt RP45") and the isogenic lasB deleted strain (which does not express LasB; "mutant RP45") cause similar mortality (in around 40% of infected mice); however the incidence of chronic colonization was significantly lower for the mutant strain in comparison to the wt counterpart (87% for the wt vs 43% for the lasB deleted strain; Fisher exact test p<0.01). This finding shows the role of LasB in establishment of chronic colonization.

Experiments were therefore conducted (1) to measure the potency of inhibition of compounds of the invention against purified *Pseudomonas aeruginosa* LasB enzyme and also experiments were conducted (2) to measure the ability of compounds of the invention to inhibit LasB-catalysed elastin degradation. The first assay uses a commercial fluorescent synthetic peptide and purified LasB enzyme. The LasB hydrolysis kinetics are measured allowing the determination of the IC50 and Ki of the inhibitors; the second is a more physiological assay using dialysed *Pseudomonas aeruginosa* supernatant as source of enzyme, plus its natural substrate Elastin. It is an "end point assay" that determines the percentage of LasB inhibition by each compound for one particular time point and inhibitor concentration. Technical details are described below:

Fluorometric Assay to Determine Ki

This assay uses commercially available substrate (Abz-Ala-Gly-Leu-Ala-p-Nitro-Benzyl-Amide (Ex: 340 nm, Em: 415 nm) from Peptide International) and purified LasB protein from *P. aeruginosa* (provided by Merck or Charles River Laboratories). It is performed to determine LasB elastase activity and assess compound inhibition in 96-well plate format. All compounds of Formula (I) were assessed using the method described below.

Method: 10 to 140 ng/ml purified LasB is incubated with 250 μM Abz-Ala-Gly-Leu-Ala-p-Nitro-Benzyl-Amide in 50 mM Tris-HCl pH 7.4, 2.5 mM CaCl2, 0.01% of Triton X100 at 37° C. LasB activity (corresponding to fluorescence emission induced by substrate hydrolysis) is measured over 30 min at 37° C. with a fluorescence plate reader such as the Perkin Elmer Envision or similar. Different range of inhibitor concentrations are routinely assessed depending of inhibitor potency from 0.0016 to 200 μM (2-fold dilutions series) in order to determine IC50.

The equation used to calculate the Ki from IC50 is: Ki=IC50/(1+([S]/Km)) where [S]=250 μM and Km=214 μM.

Elastin Assay to Determine % Inhibition

The Elastin assay uses as source of enzyme dialysed supernatant from *P. aeruginosa* PAO1 and the Elastin Congo-Red as substrate. The natural LasB substrate, elastin, is complexed with the congo-red dye (Elastin Congo-Red, ECR). The elastolysis activity from the culture supernatant will degrade elastin and release the congo-red dye into the supernatant. This red dye release can be measured with a spectrophotometer.

All compounds of Formula (I) were assessed using the method described below.

Method: To determine LasB elastase activity and assess compound inhibition, an overnight culture of *P. aeruginosa* strain PA01 is diluted in LB medium. After reaching an ° Dam. of 0.6, this culture is diluted and incubated for additional 18-24 hours in a shaking incubator. Culture supernatants are recovered by centrifugation and filtrated through a 0.22 μM filter. These supernatants are dialysed (filtration molecules <20 kDa) into a 50 mM Tris-HCl pH 7.4, 2.5 mM CaCl$_2$ solution at 4° C. under agitation for 24 hours. Supernatant dialysed is then mixed volume/volume with the ECR suspension (20 mg/mL of ECR in 100 mM Tris-HCl pH 7.4 buffer supplemented with 1 mM CaCl2) supplemented with Triton X100 (final concentration of 0.01%) in presence of DMSO (positive control) and/or different concentrations of compound (routinely 50 to 1.56 μM). As a negative control, the dialysed supernatant is replaced by Tris-HCl solution (50 mM Tris-HCl pH 7.4, 2.5 mM CaCl$_2$). The mixed reaction is then incubated overnight in a 37° C. shaking incubator. The reaction supernatant is recovered by centrifugation and the release of congo-red is measured by its absorbance at 495 nm (OD$_{495nm}$).

Percentage inhibition is determined using the following equation:

((OD$_{495nm}$ value of positive control−OD$_{495nm}$ value of negative control)−(OD$_{495nm}$ value of treated supernatant OD$_{495nm}$ value of negative control))/(OD$_{495nm}$ value of positive control−OD$_{495nm}$ value of negative control)×100.

Results are shown in the Table below and categorised into A, B and C for both assays. The Ki values are grouped as A (Ki=0.00 to 0.050 μM), B (Ki=0.05 to 0.1 μM) and C (Ki=0.1 to 10.00 μM). Similarly, for the elastase hydrolysis assay, values are grouped into A (>75% inhibition), B (60 to 75% inhibition) and C (10 to 60% inhibition) all at 25 μM inhibitor concentration. (n.d. not determined).

| Example | Ki (μM) | Elastin hydrolysis % inhibition @ 50/25 μM inhibitor concentration |
| --- | --- | --- |
| 1 | B | A |
| 2 | B | A |
| 3 | B | A |
| 4 | A | A |
| 5 | B | B |
| 6 | A | A |
| 7 | B | B |

Example 9: Inhibition of LasB-Mediated IL-1β Activation

The activity of compounds of the invention to inhibit LasB-mediated hydrolysis of pro-IL-1β to IL-1β was demonstrated using an enzymatic in vitro assay, using purified LasB and a reporter substrate (a FRET peptide mimicking the LasB IL-1β cleavage site). Hydrolysis of this FRET peptide was continuously monitored using a Victor multi-mode plate reader (Perkin Elmer) with excitation 355 nm and emission at 450 nm in the presence of varying concentrations of compounds of the invention. Inhibitory constants (Ki) were determined for certain compounds of the invention (at least 2 independent replicates) using a competitive inhibitor model. Results are shown in the table below.

| Example | Ki (LasB-mediated hydrolysis of pro-IL-1β to IL-1β)/μM |
| --- | --- |
| 4 | 0.70 |
| 6 | 0.42 |

Example 10: In Vivo Efficacy of Compounds of the Invention

Experiments were conducted to demonstrate the efficacy of compounds of the invention in treating a mouse model of *Pseudomonas aeruginosa* lung infection.

Mice were dosed by intranasal inoculation of PA (PAO1), then scarified after 24 hours. The extent of infection in the lung was quantified by bacterial load (CFU determination, colony forming units) and the levels of proinflammatory IL-1β. Statistical analysis on both readouts were performed by ANOVA with a Dunnett post-test.

Figure 2:
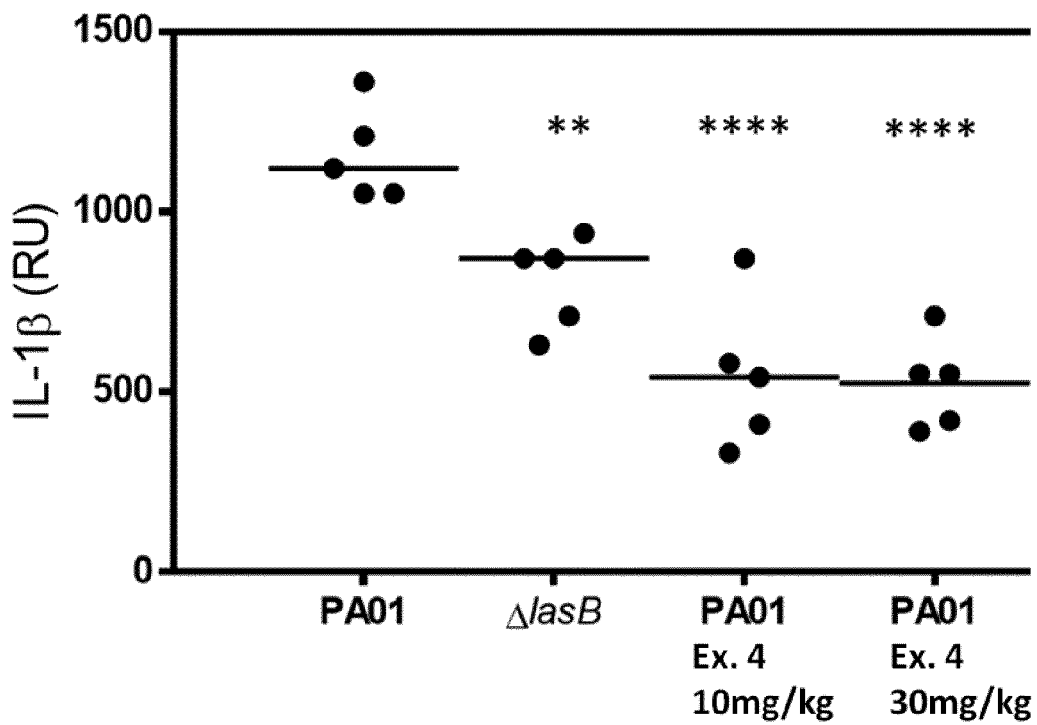
FIG. 2 shows quantification of active IL-1β in the lung following infection by wild-type and ΔlasB mutant PAO1, with and without treatment with compounds of the invention in murine lungs at 24 hours post infection. Results are discussed in Example 10.
p<0.001, **p<0.0001.
RU=relative light units, proportional to the levels of IL-1β in this experiment.
Figure 3:
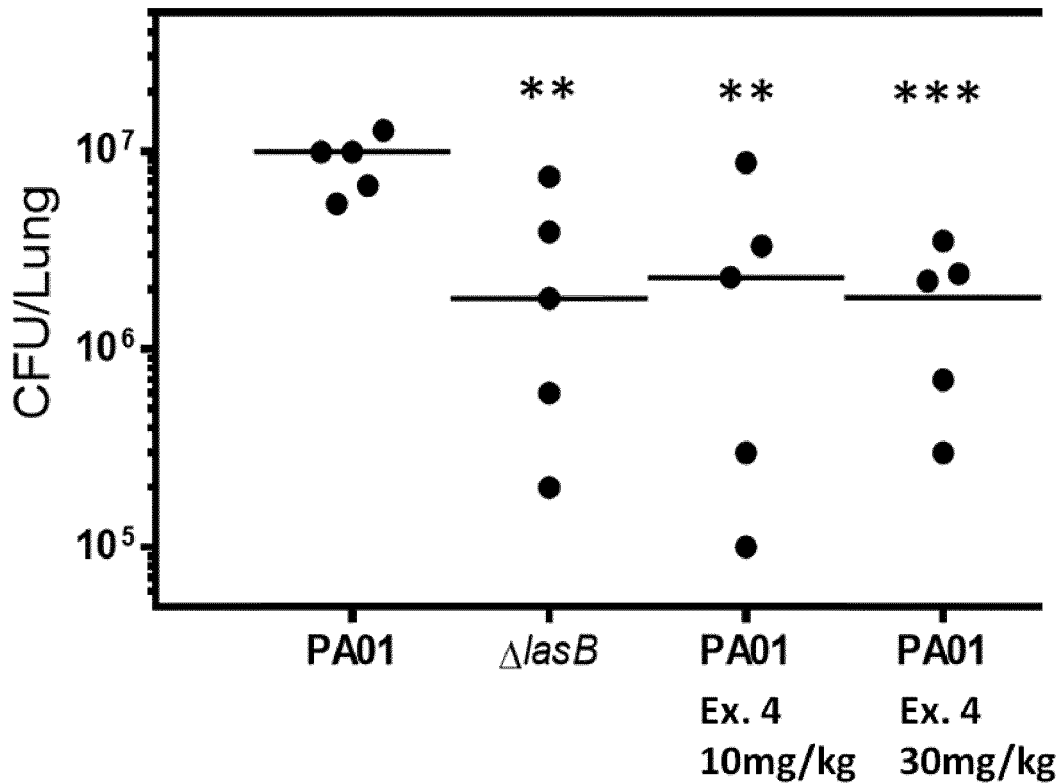
FIG. 3 shows total colony forming units of wild-type and ΔlasB mutant PAO1, with and without treatment with compounds of the invention in murine lungs at 24 hours post infection. Results are discussed in Example 10.
p<0.01, *p<0.001

Compounds were administered intravenously in a two-dose regimen (1 hour and 2 hours post infection) at two different doses (10 and 30 mg/kg). As shown in FIG. 2, the compound of Example 4 inhibited the production and activation of IL-1β in mice infected by wild-type PA (PAO1) at a similar level than the lasB deleted mutant (ΔlasB), which cannot produce LasB. As shown in FIG. 3, the compound of Example 4 reduced the extent of infection in the lung to the level of the LasB deleted mutant (ΔlasB), as determined by the CFU levels.

The invention claimed is:

1. A compound which is an indane according to Formula (I), or a pharmaceutically acceptable salt thereof,

[FORMULA (I)]

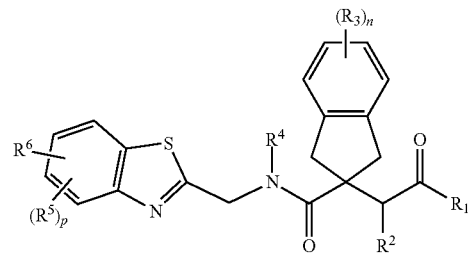

wherein
R$^1$ is selected from:
NHOH, —OH, —OR$^{1a}$ and —OCH$_2$OC(O)R$^{1a}$, wherein R$^{1a}$ is selected from an unsubstituted C$_1$ to C$_4$ alkyl group and phenyl; and
where the compound of Formula (I) contains a positively charged nitrogen atom, R$^1$ may be O$^-$, such that the compound forms a zwitterion;
R$^2$ is selected from H and unsubstituted C$_1$ to C$_2$ alkyl;
each R$^3$ group is independently selected from halogen, —OH, —NH$_2$, methyl and —CF$_3$;
n is an integer from 0 to 4;
R$^4$ is selected from H and unsubstituted C$_1$ to C$_2$ alkyl;
R$^6$ is C$_2$ to C$_4$ alkoxy which is unsubstituted or is substituted with a group selected from —OH; —NR$^{10}$R$^{11}$; —N$^+$R$^{10}$R$^{11}$R$^{12}$; —OR$^{6a}$ and —NR$^{10}$R$^{6a}$, wherein R$^{6a}$ is a C$_1$ to C$_3$ alkyl group which is unsubstituted or substituted with a group selected from OH; —NR$^{10}$R$^{11}$; —N$^+$R$^{10}$R$^{11}$R$^{12}$; —NR$^{10}$NR$^{11}$R$^{12}$; —NR$^{10}$N$^+$R$^{11}$R$^{12}$R$^{13}$; —N$^+$R$^{10}$R$^{11}$NR$^{12}$R$^{13}$; —NR$^{10}$C (NR$^{11}$) NR$^{12}$R$^{13}$; —NR$^{10}$C(N$^+$R$^{11}$R$^{12}$) NR$^{13}$R$^{14}$; —C(NR$^{10}$) NR$^{11}$R$^{12}$; and —C(N$^+$R$^{10}$R$^{11}$)NR$^{12}$R$^{13}$,
p is 0 or 1;
R$^5$ is selected from —OMe, —OH, halogen, —NR$^{10}$R$^{11}$; —N$^+$R$^{10}$R$^{11}$R$^{12}$, —CF$_3$; and $R^{10}$, $R^{11}$, $R^{12}$ $R^{13}$ and $R^{14}$ are independently H or methyl;
with the proviso that the indane of Formula (I) is other than:
2-(2-(((4-ethoxybenzo[d]thiazol-2-yl)methyl)carbamoyl)-2,3-dihydro-1H-inden-2-yl)acetic acid;
2-[2-[(6-ethoxy-1,3-benzothiazol-2-yl)methylcarbamoyl] indan-2-yl]acetic acid;
2-[2-[[6-(2-hydroxyethoxy)-1,3-benzothiazol-2-yl]methylcarbamoyl]indan-2-yl]acetic acid;
2-[2-[[6-[2-(dimethylamino)ethoxy]-1,3-benzothiazol-2-yl]methylcarbamoyl]indan-2-yl]acetic acid;
2-[2-[[6-[2-(trimethylammonio)ethoxy]-1,3-benzothiazol-2-yl]methylcarbamoyl]indan-2-yl]acetate;
2-[2-[[5-[2-(dimethylamino)ethoxy]-1,3-benzothiazol-2-yl]methylcarbamoyl]indan-2-yl]acetic acid;
2-[2-[[5-[2-(trimethylammonio)ethoxy]-1,3-benzothiazol-2-yl]methylcarbamoyl]indan-2-yl]acetate;
2-(2-(((5-(3-(dimethylamino)propoxy)-6-methoxybenzo[d]thiazol-2-yl)methyl)carbamoyl)-5,6-difluoro-2,3-dihydro-1H-inden-2-yl)acetic acid;
2-(5,6-difluoro-2-(((6-methoxy-5-(3-(trimethylammonio)propoxy)benzo[d]thiazol-2-yl)methyl)carbamoyl)-2,3-dihydro-1H-inden-2-yl)acetate; and
2-(2-(((5-(2-(dimethylamino)ethoxy)-6-methoxybenzo[d]thiazol-2-yl)methyl)carbamoyl)-2,3-dihydro-1H-inden-2-yl)acetic acid.

2. The compound of claim 1, wherein:
$R^1$ is selected from —OH and —NHOH, or where the compound of Formula (I) contains a positively charged nitrogen atom, $R^1$ may be O⁻, such that the compound forms a zwitterion;
$R^2$ is H; and/or
$R^4$ is H.

3. The compound of claim 1, wherein n is an integer from 0 to 2 and each $R^3$ group is fluorine.

4. The compound of claim 1, wherein $R^6$ is $C_2$ to $C_4$ alkoxy which is unsubstituted or is substituted with a group selected from —OH; —NR$^{10}$R$^{11}$; —N⁺R$^{10}$R$^{11}$R$^{12}$; and —OR$^{6a}$, wherein $R^{6a}$ is a $C_1$ to $C_3$ alkyl group which is unsubstituted or substituted with a group selected from OH; —NR$^{10}$R$^{11}$; and —N⁺R$^{10}$R$^{11}$R$^{12}$.

5. The compound of claim 1, wherein p is 1; and $R^6$ is $C_2$ to $C_4$ alkoxy which is substituted with a group selected from —NR$^{10}$R$^{11}$; —N⁺R$^{10}$R$^{11}$R$^{12}$; and —OR$^{6a}$, wherein $R^{6a}$ is a $C_1$ to $C_3$ alkyl group which is unsubstituted or substituted with a group selected from —NR$^{10}$R$^{11}$; and —N⁺R$^{10}$R$^{11}$R$^{12}$.

6. The compound of claim 1, wherein $R^6$ is $C_2$ to $C_4$ alkoxy which is substituted with a group selected from —OR$^{6a}$ and —NR$^{10}$R$^{6a}$, wherein $R^{6a}$ is a $C_1$ to $C_3$ alkyl group which is unsubstituted or substituted with a group selected from OH; —NR$^{10}$R$^{11}$; —N⁺R$^{10}$R$^{11}$R$^{12}$; —NR$^{10}$NR$^{11}$R$^{12}$; —NR$^{10}$N⁺R$^{11}$R$^{12}$R$^{13}$; —N⁺R$^{10}$R$^{11}$NR$^{12}$R$^{13}$; —NR$^{10}$C(NR$^{11}$)NR$^{12}$R$^{13}$; —NR$^{10}$C(N⁺R$^{11}$R$^{12}$) NR$^{13}$R$^{14}$; —C(NR$^{10}$) NR$^{11}$R$^{12}$; and —C(N⁺R$^{10}$R$^{11}$) NR$^{12}$R$^{13}$.

7. The compound of claim 1, wherein $R^6$ is $C_2$ to $C_4$ alkoxy which is substituted with a group —OR$^{6a}$, wherein $R^{6a}$ is a $C_1$ to $C_3$ alkyl group which is unsubstituted or substituted with a group selected from OH; —NR$^{10}$R$^{11}$; and —N⁺R$^{10}$R$^{11}$R$^{12}$.

8. The compound of claim 1, which is
2-[5,6-difluoro-2-[[6-methoxy-5-[2-[2-(trimethylammonio)ethoxy]ethoxy]-1,3-benzothiazol-2-yl]methylcarbamoyl]indan-2-yl]acetate or a pharmaceutically acceptable salt thereof;
2-[2-[[6-methoxy-5-[3-(trimethylammonio)propoxy]-1,3-benzothiazol-2-yl]methylcarbamoyl]indan-2-yl]acetate or a pharmaceutically acceptable salt thereof; or
2-[2-[[6-methoxy-5-[2-[2-(trimethylammonio)ethoxy]ethoxy]-1,3-benzothiazol-2-yl]methylcarbamoyl]indan-2-yl]acetate or a pharmaceutically acceptable salt thereof.

9. The compound of claim 1, which is
2-[2-[[6-(3-hydroxypropoxy)-1,3-benzothiazol-2-yl] methylcarbamoyl]indan-2-yl]acetic acid;
2-[2-[(6-propoxy-1,3-benzothiazol-2-yl)methylcarbamoyl]indan-2-yl]acetic acid;
2-[2-[[5-[3-(dimethylamino)propoxy]-6-methoxy-1,3-benzothiazol-2-yl]methylcarbamoyl]indan-2-yl]acetic acid;
2-[5,6-difluoro-2-[[6-methoxy-5-[2-(trimethylammonio)ethoxy]-1,3-benzothiazol-2-yl]methylcarbamoyl]indan-2-yl]acetate;
2-(2-(((5-(4-(dimethylamino) butoxy)-6-methoxybenzo[d]thiazol-2-yl)methyl)carbamoyl)-2,3-dihydro-1H-inden-2-yl)acetic acid;
2-(2-(((6-methoxy-5-(4-(trimethylammonio) butoxy) benzo[d]thiazol-2-yl)methyl)carbamoyl)-2,3-dihydro-1H-inden-2-yl)acetate;
or a pharmaceutically acceptable salt thereof.

10. A pharmaceutical composition comprising (i) the compound of claim 1 and (ii) at least one pharmaceutically acceptable carrier or diluent.

11. The pharmaceutical composition of claim 10, further comprising (iii) an antibiotic agent.

12. The pharmaceutical composition of claim 11, wherein the antibiotic agent is selected from tobramycin, neomycin, streptomycin, gentamycin, ceftazidime, ticarcillin, piperacillin, tazobactam, imipenem, meropenem, rifampicin, ciprofloxacin, amikacin, colistin, aztreonam, azithromycin and levofloxacin.

13. A combination of (i) the compound of claim 1 and (ii) an antibiotic agent.

14. The combination of claim 13, wherein the antibiotic agent is selected from tobramycin, neomycin, streptomycin, gentamycin, ceftazidime, ticarcillin, piperacillin, tazobactam, imipenem, meropenem, rifampicin, ciprofloxacin, amikacin, colistin, aztreonam, azithromycin and levofloxacin.

* * * * *